Figure 1:
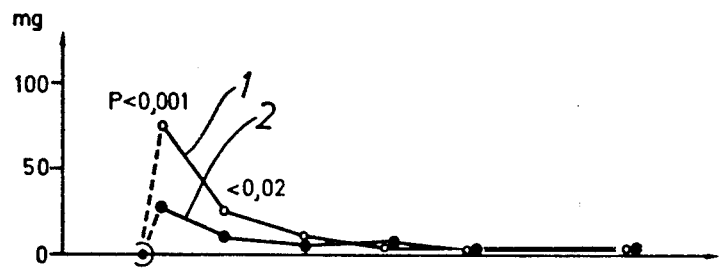

United States Patent [19]

Frommer et al.

[11] B 4,013,510
[45] * Mar. 22, 1977

[54] GLYCOSIDE-HYDROLASE ENZYME INHIBITORS

[75] Inventors: Werner Frommer; Walter Puls, both of Wuppertal-Elberfeld; Dietmar Schafer, Neuhof near Fulda; Delf Schmidt, Wuppertal-Vohwinkel, all of Germany

[73] Assignee: Farbenfabriken Bayer Aktiengesellschaft, Leverkusen, Germany

[ * ] Notice: The portion of the term of this patent subsequent to Apr. 8, 1992, has been disclaimed.

[22] Filed: July 31, 1974

[21] Appl. No.: 493,463

[44] Published under the second Trial Voluntary Protest Program on March 23, 1976 as document No. B 493,463.

Related U.S. Application Data

[62] Division of Ser. No. 213,066, Dec. 28, 1971, Pat. No. 3,876,766.

[30] Foreign Application Priority Data

Dec. 28, 1970 Germany .......................... 2064092

[52] U.S. Cl. ........................... 195/31 R; 195/80 R; 424/181; 426/321
[51] Int. Cl.² ......................................... C12B 13/00
[58] Field of Search ................. 195/80 R, 31 R, 81, 195/104, 96; 260/112.5 R; 426/321; 424/115, 180, 181

[56] References Cited

UNITED STATES PATENTS 3,127,315  3/1964  Tardrew et al. ................. 421/115
3,629,404  12/1971  Florent et al. ................... 195/80 R

OTHER PUBLICATIONS

Niwa et al., "Nojirimycin," as a Potent Inhibitor of Glucosidase," Agr. Biol. Chem., Vol. 34, No. 6, pp. 966–968, (1970).

Primary Examiner—A. Louis Monacell
Assistant Examiner—Thomas G. Wiseman
Attorney, Agent, or Firm—Depaoli & O'Brien

[57] ABSTRACT

This invention relates to inhibitors for glycosidehydrolases derived from bacteria of the order Actinomycetales, means for their production comprising cultivation of a microorganism of the order Actinomycetales in appropriate nutrient solutions under conditions most favorable to growth and production of the enzyme inhibitor and recovering, as a new product, glycoside-hydrolase enzyme inhibitors, from the culture as well as the use of said enzyme inhibitors in pharmaceutically acceptable therapeutic compositions in the treatment of conditions indicating obesity, diabetes, pre-diabetes, gastritis, gastric ulcer, hyperlipidemia (arteriosclerosis) and the like. The invention also contemplates the provision of methods of inhibiting the reaction of carbohydrates and glycoside-hydrolase enzymes and particularly carbohydrate-splitting glycoside-hydrolase enzymes of the digestive tract by means of conducting said reaction of said carbohydrates and glycoside-hydrolase enzymes in the presence of a glycoside-hydrolase enzyme inhibitor for said glycoside-hydrolase enzyme derived from a strain of microorganism of the order Actinomycetales. The invention further contemplates the provision of methods for the treatment of indications of the group consisting of obesity, adipose, hyperlipidemia (arteriosclerosis), diabetes, pre-diabetes, gastritis, gastric ulcer, duodenal ulcer, and caries induced by the action of glycoside-hydrolase enzymes and carbohydrates, the improvement which comprises employing an enzyme inhibitor for glycoside-hydrolase enzymes produced by a strain of microorganism of the order Actinomycetales.

1 Claim, 6 Drawing Figures

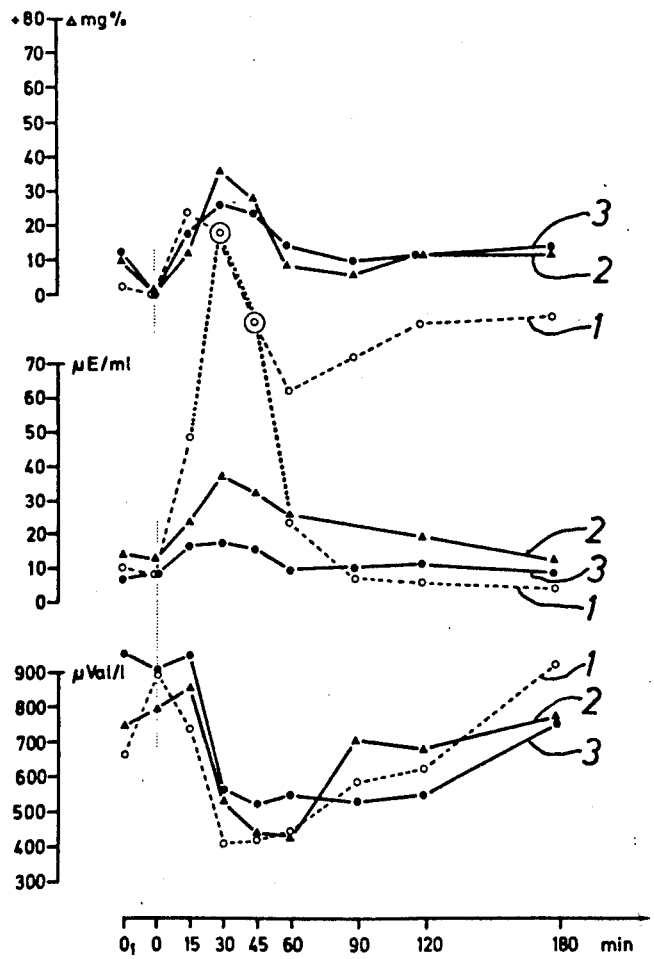

GLYCOSIDE-HYDROLASE ENZYME INHIBITORS

This is a division of application Ser. No. 213,066 filed Dec. 28, 1971, now U.S. Pat. No. 3,876,766.

BACKGROUND OF THE INVENTION

Carbohydrates are eaten either as simple sugars or as more complex molecules called polysaccharides, which are built up from simple sugar units and of which the starch of potatoes, bread, etc., is a well-known example. The body absorbs carbohydrates from the small intestine in the form of single sugar units, or monosaccharides. Those sugars which are ingested in this form, e.g., glucose in various "energy-giving" preparations and fructose, the sugar of fruit, thus require no further treatment. Sugar molecules bigger than this require enzymic digestion.

The digestion of starch begins in the mouth. Saliva contains an enzyme, amylase, which attacks starch and similar polysaccharides, reducing the size of the molecule. Starch is made up of chains of glucose molecules linked in a particular way, and amylase attacks the links between the glucose units. The enzyme acts at many points in the chain, and the smallest units it produces are molecules of the sugar maltose. Maltose is made up of two glucose units; this sugar is thus a disaccharide.

The dextrins resulting from the "pruning" by amylase are attacked by an enzyme in the small intestine which can break the inter-chain links. A specific enzyme, maltase, also splits each molecule of maltose produced from starch into two molecules of glucose, which are then absorbed and metabolized by the body. Some of the sugars of food are disaccharides; common sugar (sucrose) is made up of a molecule of glucose joined to a molecule of fructose, and lactose (the sugar of milk) is also a disaccharide. These sugars are split into their component monosaccharides by specific enzymes in the intestine.

However, in the treatment of conditions in which there is an indication of obesity, adipose, hyperlipidemia (arteriosclerosis), diabetes, pre-diabetes, gastritis, gastric ulcer, duodenal ulcer, and/or caries, it is necessary that such glycosidehydrolase enzyme be inhibited or suppressed in such a manner that they cannot further catalyze the breakdown thereof, as indicated in the manner above for subsequent utilization by the body and thus further promotion or worsening of the condition being treated.

It has been known heretofore that $\alpha$-amylases can be inhibited by the use of various low molecular substances, such as, for example, salicylic acid and abiscisin [T. Hemberg, J. Larsson, Physiol. Plant. 14, 861 (1961), T. Hemberg, Acta Chem. Scand. 21, 1665

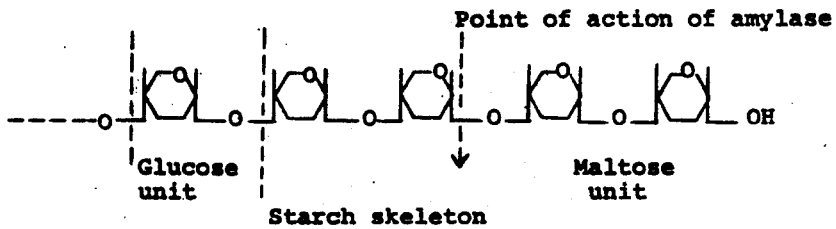

Starch also contains branched chains of glucose units, and the amylase of saliva cannot break the chains at the points where branching occurs:

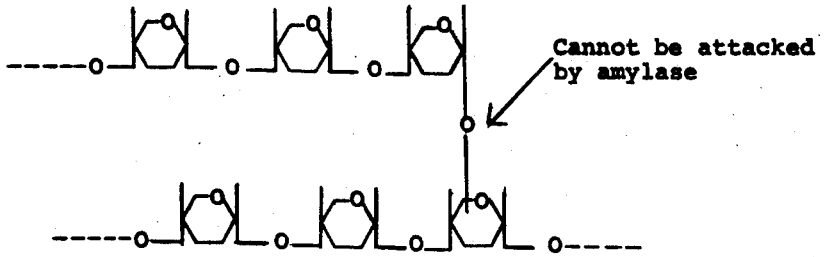

If the branched-chain structure of starch is thought of as resembling a bush, the enzyme can prune the outer branches until it reaches a fork and then its action stops. Thus, as well as molecules of maltose, amylase produces from starch fragments of the original molecule which are like hard-pruned bushes and which are called "limit dextrins". Glycogen, the carbohydrate storage material of animal tissues, is also made up of much-branched chains of glucose units.

The digestion of starch or glycogen by salivary amylase probably does not get very far, however. The process continues for a while after the food has entered the stomach, but as the acid of the gastric juice penetrates through the food mass the amylase action slows down and stops. The main attack on these polysaccharides takes place in the small intestine by an amylase in pancreatic juice similar to that in saliva.

(1967)]. It is further known that there are also higher-molecular substances which are capable of inhibiting the activity of certain amylases non-specifically by physical adsorption [T. Chrzaszcz, J. Janicki, Bioch. Z. 260, 354 (1933) and Bioch. J. 28, 296 (1934)] or by denaturation and precipitation of the enzyme [B. S. Miller, E. Kneen, Arch. Biochem. 15, 251 (1947), D, H. Struhmeyer, M. H. Malin, Biochem. Biophys. Acta 184, 643 (1969)]. It has also been observed that it is possible to elute a substance from wheat by means of distilled water, which lowers the dextrifying activity of salivary amylase but has little influence on the activity of pancreatic amylase [E. Kneen, R. M. Sandstedt, Arch., Bioch. 9, 235 (1946)].

It is a disadvantage of these known inhibitors that either the inhibition of the amylase is non-specific or that the inhibiting activity of the inhibitor is slight, especially on pancreatic amylases, as has been shown by our own investigations; that is to say, only at very high ratios of inhibitor: enzyme is almost complete inhibition of the amylases (up to 90% and above) attained.

An earlier proposal (United States patent application Ser. No. 110,482, filed Jan. 28, 1971, now abandoned) relates to amylase inhibitors. In fact, the older proposal shows that by means of aqueous electrolyte solutions, preferably dilute acids, or above all by means of water-alcohol ($C_1$–$C_3$ -alcohols) mixtures, preferably at acid pH values, a highly active inhibitor for pancreatic amylase, which does not show the disadvantages mentioned, can be extracted in high yields from wheat (coarse ground wheat, wheat flour or wheat gluten). The substance thus obtained inhibits pancreatic amylase to the extent of more than 90% even at very low inhibitor:enzyme ratios.

THE PRESENT INVENTION

The present invention now relates to inhibitors for glycoside-hydrolases from actinomycetes, and in particular to inhibitors for glycoside-hydrolases of preferably carbohydrate-splitting enzymes of the digestive tract from actinomycetes. These inhibitors are formed by microorganisms of the order Actinomycetales, especially by those of the family of Streptomycetaceae, Thermoactinomycetaces, Micromonospora, Nocardia, and above all those of the family Actinoplanaceae. They are also formed to a particularly high degree by strains of the genera *Actinoplanes, Ampullariella, Streptosporangium, Streptomyces, Chainia, Pilimelia, Planomonospora*, and *Actinobifida*.

Accordingly, this invention provides, as a new product, a glycoside-hydrolase inhibitor of microbial origin.

This invention further provides a method for the production of a glycoside-hydrolase inhibitor comprising culturing a microbe of the order Actinomycetales and extracting the inhibitor from the resultant culture.

The preferred microorganisms are preferably of the family Streptomycetaceae or Actinoplanaceae.

A wide variety of microorganisms of the order Actinomycetales have been found to be glycoside-hydrolase enzyme inhibitors and the methods described below can be used to test the microorganisms to determine whether or not the desired glycoside-hydrolase enzyme inhibitor activity is present and the approximate relative value of this activity.

Strains of the order Actinomycetales, especially those of the families Streptomycetaceae and Actinoplanaceae, are isolated in a known manner from samples of soil or strains of those orders bought from culture collections. Culture flasks containing nutrient solutions which permit the growth of these strains are inoculated with inoculum of these strains. For example, the glycerine-glycine nutrient solution according to von Plotho, of composition 2% glycerine, 0.25% glycine, 0.1% NaCl, 0.1% $K_2HPO_4$, 0.01% $FeSO_4$, 0.7 $H_2O$, 0.01% $MgSO_4$, 0.7 $H_2O$ and 0.1% $CaCO_3$ can be used. For more rapid growth, it is advisable also to add to such a nutrient solution complex sources of carbon, such as, for example, corn-steep liquor or soya flour or yeast extract or protein hydrolysates, for example NZ-amines, or mixtures of these substances. In these cases, the pH value of the solution must be adjusted. An initial pH of the nutrient solution of between 6.0 and 8.0, especially between 6.5 and 7.5, is preferred.

The glycerine of the nutrient solution can also be replaced by other sources of carbon, such as, for example, glucose or sucrose or starch or mixtures of these substances. Instead of glycine, it is also possible to use other sources of nitrogen, such as, for example, yeast extract, soya flour, NZ-amines, pharmamedia and others. The concentrations of the sources of carbon and nitrogen, and also the concentrations of the salts, can vary within wide limits. $FeSO_4$, $CaCO_3$ and $MgSO_4$ can also be entirely absent. 100–200 ml, for example, of the nutrient solution are introduced into 1 liter Erlenmeyer flasks, sterilized in a known manner and inoculated with the strain to be investigated, and the flask is incubated on shaking machines at 15°–60°C., preferably at 24°–50°C. If the culture shows growth, which generally takes place after 1–10 days, and in most cases after 3–5 days, a sample of, for example 5 ml is taken and the mycelium in this sample is separated off by filtration or centrifugation. 0–100 μl of the culture broths are employed in the tests described below, and the inhibiting capacity per ml is calculated.

The mycelia are extracted twice with 5 volumes (relative to the volume of mycelium) of acetone at a time, and subsequently 1 × 5 volumes of diethyl ether, the extracted mycelium residue is dried in vacuo at 20° and the resulting dry mycelium powder is extracted with 4–8 parts by weight of dimethyl sulphoxide (DMSO).

The two acetone extracts and the ether extracts are combined and concentrated almost to dryness in vacuo. The residue from these extracts is taken up with the dimethyl sulphoxide (DMSO) extract from the dry powder and 0–100 μl thereof are employed in the tests described below.

AMYLASE TEST

One amuylase inhibitor unit (1 AIU) is defined as the amount of inhibitor which inhibits two amylase units to the extent of 50%. one amylase unit (AU) is the amount of enzyme which in 1 minute, under the test conditions indicated below, splits 1 μ equivalent of glucoside bonds in starch. The μVal of split bonds are determined colorimetrically as μVal of reducing sugar formed, by means of dinitrosalicylic acid, and are specified as μVal of maltose equivalents by means of a maltose calibration curve. To carry out the test, 0.1 ml of amylase solution (20–22 AU/ml) are treated with 0–400 ug of inhibitor or 0–100 μl of the culture solution or mycelium extracts to be tested, in 0.4 ml of 0.02 M sodium glycerophosphate buffer/0.001 M $CaCl_2$ pH 6.9, and the mixture is equilibrated in a waterbath at 35°C. for about 10–20 minutes. It is then incubated for 5 minutes at 35°C. with 0.5 ml of a 1% strength starch solution (soluble starch of Messrs. Merck, Darmstadt, No. 1252) which has been pre-warmed to 35°C., and is subsequently treated with 1 ml of dinitrosalicylic acid reagent (according to P. Bernfeld in Colowick-Kaplan, Meth. Enzymol., volume 1, page 149). To develop the color, the batch is heated for 5 minutes on a boiling waterbath and then cooled and treated with 10 ml of distilled water. The extinction at 540 nm is measured against an appropriately mixed blank, without amylase. For evaluation, the amylase activity which is still active after addition of the inhibitor is read off from a previously recorded amylase calibration curve, and the percentage inhibition of the amylase employed is calculated therefrom. The percentage inhibition is plotted as a function of the quotient:

$$\frac{\mu g \text{ of inhibitor } +}{AU ++}$$

(+ relative to solids, ++ AU in the non-inhibited mix of the same series), and the 50% inhibition point is read off from the curve and converted to AIU/mg of inhibitor.

SACCHARASE TEST

One saccharase inhibitor unit (SIU) is defined as the amount of inhibitor which inhibits two saccharase units to the extent of 50%. One saccharase unit (SU) is the amount of enzyme which in one minute, under the test conditions indicated below, splits 1 $\mu$mol of sucrose into glucose and fructose. The $\mu$mol of split sucrose are determined colorimetrically as the glucose and fructose formed, by means of dinitrosalicylic acid, and calculated by means of a glucose/fructose calibration curve.

To carry out the test, 0.1 ml of saccharase solution comprising a solubilized saccharase from intestinal mucous membrane of pigs, [according to B. Borgstrom, A. Dahlquist, Acta Chem. Scand. 12, (1958) page 1997] in the amount of 0.3–0.4 SU/ml are mixed with 0–400 $\mu$g of inhibitor or 0–50 $\mu$l of the culture solution of the mycelium extract which is to be investigated, in 0.1 ml of a 0.1 M Na maleate buffer of pH 6.0, and the mixture is equilibrated for about 10–20 minutes in a waterbath at 35°C. It is then incubated for 60 minutes at 35°C. with 0.2 ml of an 0.056 M sucrose solution (sucrose: Messrs. Merck, Darmstadt, No. 7652) which has been pre-warmed to 35°C., and is subsequently treated with 0.5 ml of dinitrosalicylic acid reagent (according to P. Bernfeld in Colowick-Kaplan. Meth. Enzymol., Volume 1, page 149). To develop the color, the mix is heated for 5 minutes on a boiling waterbath and then cooled and treated with 5 ml of distilled water. The extinction at 540 nm is measured against an appropriate blank value without saccharase.

For evaluation, the saccharase units which are still active after addition of inhibitor are determined from the calibration curve and the percentage inhibition of the saccharase employed is calculated therefrom. The percentage inhibition is plotted as a function of the quotient:

$$\frac{\mu g \text{ of inhibitor } +}{SU ++}$$

(+ relative to solids, ++ SU in non-inhibited mix of the same series), and the 50% inhibition point is read off from the curve and converted to SIU/mg of inhibitor.

MALTASE TEST

One maltase inhibitor unit (1 MIU) is defined as the amount of inhibitor which inhibits two maltase units to the extent of 50%. One maltase unit (MU) is the amount of enzyme which in 1 minute, under the test conditions indicated below, splits 1 $\mu$ equivalent of glucosidic bond in the p-nitrophenyl-$\alpha$-D-glucopyranoside. The $\mu$Val of split bonds are determined photometrically, as $\mu$Val of p-nitrophenolate.

To carry out the test, 0.05 ml of maltase solution comprising a solubilized maltase from intestinal mucous membrane of pigs [according to B. Borgstrom, A. Dahlquist, Acta Chem. Scand. 12, (1958), page 1997], or maltase in the form of human pancreatic juice lyophilizate, (0.09–0.12 MU/ml) are equilibrated with 0–400 $\mu$g of inhibitor or 0–20 $\mu$l of the culture solution to be investigated or of the mycelium extract in 0.05 ml of 0.1 M sodium maleate buffer at pH 6.0 for about 10–20 minutes in a waterbath at 35°C. The mixture is then incubated for 30 minutes at 35°C. with 0.1 ml of an 0.4% strength solution of p-nitrophenyl-$\alpha$-D-glucopyranoside (Messrs. Serva, Heidelberg, No. 30,716) in 0.1 M Na maleate buffer at pH 6, which has been pre-warmed to 35°C., and the reaction is subsequently stopped by adding 2 ml of 0.565 M tris-buffer of pH 7.6. The extinction at 403 nm is immediately measured against an appropriately mixed blank without maltase.

For evaluation, the maltase units still active after addition of inhibitor are calculated on the basis of a molar extinction coefficient of $E_{403} = 13.2 \times 10^3$ for the p-nitrophenolate anion at pH 7.6, and from the maltase units still active the percentage inhibition of the maltase employed is calculated. The percentage inhibition is plotted as a function of the quotient:

$$\frac{\mu g \text{ of inhibitor } +}{MU ++}$$

(+ relative to solids, ++ MU in the non-inhibited mix) and the 50% inhibition point is read off from the curve and converted to MIU/mg of inhibitor.

Since, in this simple routine test, an artificial substrate and not the actual substrate of maltase (maltose) is used, the preparations are additionally tested for their maltase-inhibiting activity in a more involved maltase test described by Dahlquist (Enzyme. biol. clin. 11, 52/1970). Herein, the glucose produced during the action of maltase on maltose is measured enzymatically by means of colorimetry, using glucose oxidase, peroxidase and dianisidine. All the maltase inhibitors described here also inhibit in this test.

A whole series of strains of various families and genera of the order Actinomycetales was tested in accordance with the method described above. In doing so, distinct, though at times weak, glycoside-hydrolase-inhibiting activities were found in various families and genera. The strains of the family of the Streptomycetaceae and especially of the family of the Actinoplanaceae proved most advantageous as regards yield.

Within these families, particularly active strains were found in the genera *Streptomyces*, *Actinoplanes*, *Ampullariella* and *Streptosporangium*. Of the strains tested, those listed below proved particularly active in one or more of the tests indicated.

Table 1

| Strain No. | | Name | Inhibiting Action Amylase Maltase Saccharase | | | | | |
|---|---|---|---|---|---|---|---|---|
| Own Designation | Collection Nos. | | C | M | C | M | C | M |
| SB 2 | CBS 951.70 | Ampullariella regularis | +++ | + | | | | |
| SB 5 | CBS 952.70 | " | +++ | | | | | |
| SB 11 | CBS 955.70 | Actinoplanes spec. | | | +++ | +++ | | |
| SB 12 | CBS 956.70 | " | +++ | | | | | |

Table 1-continued

| Strain No. Own Designation | Collection Nos. | Name | Inhibiting Action Amylase | | Maltase | | Saccharase | |
|---|---|---|---|---|---|---|---|---|
| | | | C | M | C | M | C | M |
| SB 18 | CBS 957.70 | " | +++ | +++ | + | ++ | ++ | ++ |
| SB 27 | CBS 958.70 | " | +++ | | | | | |
| SB 46 | CBS 959.70 | " | +++ | | | | | |
| SE 5 | CBS 960.70 | Actinoplanes spec. | | | ++ | ++ | | |
| SE 21 | CBS 953.70 | Ampullariella regularis | +++ | | | | | |
| SE 39 | CBS 954.70 | " | +++ | | | | | |
| SE 50 | CBS 961.70 | Actinoplanes spec. | +++ | ++ | +++ | ++ | +++ | ++ |
| SE 55 | CBS 962.70 | " | ++ | + | ++ | ++ | ++ | ++ |
| SS 26 | CBS 963.70 | Streptosporangium album | | | | ++ | | |
| SS 45 | CBS 964.70 | " spec. | | | | ++ | | |
| SS 51 | CBS 965.70 | " | | | ++ | ++ | | |
| SS 53 | CBS 966.70 | " roseum | | | ++ | ++ | | |
| St 19 | ATCC 3319 | Streptomyces flaveolus | ++ | | | | | |
| St 50 | CBS 693.69 | Streptomyces heimii | | | | | + | |
| St 67 | CBS 432.59 | Streptomyces tendae | | | ++ | | ++ | |
| St 45 | CBS 434.51 | Streptomyces aureofaciens | | | + | | | |
| RT 36 | CBS 228.65 | Chainia rubra | | | + | | | |
| RT 33 | CBS 295.66 | Chainia poonensis | | | + | | | |
| ST 12 | NRRL B-2286 | Streptomyces murinus | +++ | | + | | | |
| ST 51 | CBS 498.68 | Streptomyces fradiae | ++ | | | | | |
| ST 3 | NRRL 2580 | Streptomyces chrysomallus | ++ | | | | | |
| ST 1 | ATCC 11523 | " | ++ | | | | | |
| SS 55 | CBS 624.71 | Streptosporangium roseum | | ++ | | | | |
| SS 59 | " 623.71 | " amethystogenes | | ++ | | | | |
| SS 62 | " 625.71 | " roseum | | ++ | | | | |
| AT 8 | KCC-A 0027 | " viridalbum | | ++ | | | | |
| AT 11 | KCC-A 0025 | " album | | ++ | | | | |
| AT 13 | CBS 19064 | Ampullariella campanulata | +++ | | | | | |
| AT 14 | CBS 19364 | Ampullariella regularis | +++ | | | | | |
| SE 89 | CBS 619.71 | Ampullariella spec. | | +++ | | | | |
| SE 100 | CBS 622.71 | Planomonospora spec. | ++ | ++ | | | | |
| AT 4 | CBS 191.64 | Ampullariella digitata | | | + | | ++ | |
| At 9 | KCC-A 0028 | Streptosporangium vulgare | | | | + | ++ | ++ |
| AT 10 | ATCC 19190 | " indianensis | | | | | ++ | ++ |
| SE 103 | CBS 616.71 | Actinoplanes spec. | | | | | | ++ |
| HN 6 | CBS 602.71 | Actinobifida chromogena | | | | | | ++ |
| HN 2 | CBS 601.71 | " | | | | | | +++ |
| AT 2 | CBS 367.66 | Actinoplanes utahensis | | | + | | | |
| SE 101 | CBS 621.71 | Planomonospora parontospora | | | | + | | |
| SK 2 | CBS 620.71 | Pilimelia spec. | | | | + | | ++ |
| SE 82 | CBS 615.71 | Actinoplanes spec. | +++ | +++ | ++ | ++ | ++ | ++ |
| SA 28 | CBS 617.71 | Ampullariella digitata | | | + | + | | |
| SA 8 | CBS 611.71 | Actinoplanes spec. | +++ | | | | | |
| AT 7 | ATCC 12428 | Streptosporangium roseum | | ++ | | | | |

Table 1-continued

| Strain No. Own Designation | Collection Nos. | Name | Inhibiting Action Amylase | | Maltase | | Saccharase | |
|---|---|---|---|---|---|---|---|---|
| | | | C | M | C | M | C | M |
| SE 45 | CBS 618.71 | Ampullariella regularis | | | | | | + |

ATCC = American Type Culture Collection
CBS = Centraalbureau voor Schimmelcultures, Baarn
NRRL = Culture Collection Unit, Fermentation Section, Norther Utilization Research Branch, Peoria, Illinois, USA
KCC = Culture Collection, Research Division, Kaken Chemical Co., Ltd., Tokyo, Japan
C = Culture solution
M = Mycelium extract
+ = distinctly active
++ = strongly active
+++ = very strongly active

Table 2

| | Streptosporangium album SS 26 | Streptosporangium spec. SS 45 | Streptosporangium spec. SS 51 |
|---|---|---|---|
| Date of isolation | August 2, 1967 | November 8, 1968 | November 9, 1968 |
| Method | soil smear, plate | soil smear, plate | soil smear, plate |
| Origin | Rhon, Heidelstein, turf soil between basalt blocks, pH 3.9 | Kenya, near Ruiru, coffee plantation, pH 5.4 | Kenya, near Ruiru, coffee plantation, pH 5.4 |
| Mycelium AM | white | white—cream—yellowish or pink | white—cream—yellowish or pink |
| SM | 0.5–1.2 $\mu$, septate | 0.4–1.2 $\mu$ | 0.4–1.2 $\mu$, septate |
| Shape of Sporangia | spherical, in part wrinkled and deformed | spherical, smooth | spherical, smooth, some also wrinkled and irregular, shriveled forms |
| Size of Sporangia | 3–7 $\mu$ $\phi$ | 3–11 $\mu$ $\phi$ | 3–11 $\mu$ $\phi$ |
| Shape of Spores | ± spherical to elongated | mostly ± oval | mostly ± oval, in parts spherical |
| Size of Spores | 0.6–0.9 × 0.6–1.3 $\mu$ | 0.7–1.1 × 1.0–1.7 $\mu$ | 0.7–1.0 × 0.8–1.7 $\mu$ |
| Flagellation | − | − | − |
| Arrangement of Spores in Sporangium | spiral chains | spiral chains | spiral chains |
| Conidia, Substrate spores and the like | | | |
| Melanine | PEH − / CPC − / Ty − / Gel − } − | PEH − / CPC − / Ty − / Gel − } − | PEH − / CPC − / Ty − / Gel − } − |
| Nitrate reduction | + (weak) | − | − |
| Gelatine liquefaction | + | + | + |
| Milk peptonization | + | | |
| Growth at 20°C. | + | + | + |
| 26°C. | ++ | ++ | ++ |
| 32°C. | ++ | + | +(+) |
| 37°C. | − | + | + |
| 42°C. | − | − | − |
| NaCl toleration 2% | + slight growth | ++ | ++ |
| 3% | − | ++ | ++ |
| 4% | − | + | + |
| 7% | − | − | − |
| Starch hydrolysis | − | + | + |

| | Streptosporangium roseum SS 53 | Actinoplanes spec. SE 5 | SE 55 |
|---|---|---|---|
| Date of isolation | November 9, 1968 | December 16, 1969 | December 31, 1969 |
| Method | soil smear, plate | pollen | pollen |
| Origin | Kenya, near Ruiru coffee plantation, pH 5.7 | Kenya, near Ruiru coffee plantation, pH 5.6 | Kenya, Njoro, Eldoret Experimental Station, pH 5.1 |
| Mycelium AM | pink | 0.4–1.3 $\mu$ | 0.3–1.3 $\mu$, septate |
| SM | 0.4–1.2 $\mu$ | | |
| Shape of Sporangia | spherical, in part slightly wrinkled | | irregular |
| Size of Sporangia | 3–10 $\mu$ $\phi$ | | about 4–12 $\mu$ |
| Shape of Spores | mostly ± oval | | ± spherical |
| Size of Spores | 0.7–1.1 × 1.0–1.9 $\mu$ | | Ca. 1 $\mu$ |
| Flagellation | − | | |
| Arrangement of Spores in Sporangium | spiral chains | | coiled chains; spore chains also in places running parallel and straight |
| Conidia, Substrate spores and the like | | on CPC: substrate spores, mostly spherical (±), up to approx. 2 $\mu$ $\phi$ individual or several together, terminal or intercalar | |
| Melanine | PEH − | | |

Table 2-continued

|  | Streptosporangium roseum SS 53 | Actinoplanes spec. SE 5 | SE 55 |
|---|---|---|---|
|  | CPC −<br>Ty −<br>Gel − | CPC −<br>Ty − | CPC +<br>Ty + |
| Nitrate reduction | + |  |  |
| Gelatine liquefaction | + |  |  |
| Milk peptonization | + | − | − |
| Growth at 20°C. |  |  | ++ |
| 26°C. | ++ |  | ++ |
| 32°C. | ++ |  | ++ |
| 37°C. | + |  | ++ |
| 42°C. | − |  | − |
| NaCl 2% | +(+) |  |  |
| toleration 3% | + |  |  |
| 4% | − |  |  |
| 7% | − |  |  |
| Starch hydrolysis | + |  | + |

|  | Ampullariella regularis SB 2 | Ampullariella regularis SB 5 | Ampullariella regularis SE 21 |
|---|---|---|---|
| Date of isolation | July 2, 1966 | July 3, 1966 | December 17, 1969 |
| Method | pollen | pollen | pollen |
| Origin | Neuhof, Fulda district, soil under rotted straw, edge of field, pH 5.7 | Neuhof, Fulda district, soil under rotted straw, edge of field, pH 5.7 | Kenya, near Ruiru coffee plantation, pH 5.3 |
| Mycelium | 0.3–1 $\mu$, broad | 0.3–1 $\mu$ | 0.3–1 $\mu$ |
| Shape of Sporangia | bottle-shaped, cylindrical, "money-pouch-shaped" | bottle-shaped, cylindrical, "money-pouch-shaped" | bottle-shaped, cylindrical, "money-pouch-shaped" |
| Size of Sporangia | 4–10 × 7–18 $\mu$ | 3.5–7 × 6–14 $\mu$ | 3.5–9 × 6–13 $\mu$ |
| Shape of Spores | small rods | small rods | small rods |
| Size of Spores | 0.5–0.7 × 1.5–2.2 $\mu$ | 0.5–0.7 × 1.5–2.2 $\mu$ | 0.5–0.7 × 1.5–2.2 $\mu$ |
| Flagellation | lophotrichous | lophotrichous | lophotrichous |
| Arrangement of Spores in Sporangium | linear parallel chains | linear parallel chains | linear parallel chains |
| Conidia, Substrate spores and the like |  |  |  |
| Melanine | CPC −<br>Ty −<br>Gel − | CPC −<br>Ty −<br>Gel − | CPC +<br>Ty + |
| Nitrate reduction | + | + |  |
| Gelatine liquefaction | + | + |  |
| Milk peptonization | + | + | + |
| Starch-hydrolysis | + | + | + |
| Growth at 20°C. | ++ | ++ | ++ |
| 26°C. | ++ | ++ | ++ |
| 32°C. | ++ | ++ | ++ |
| 37°C. | − | − | ++ |
| 42°C. | − | − | − |

|  | Ampullariella regularis SE 39 | Actinoplanes spec. SB 11 | Actinoplanes spec. SB 12 |
|---|---|---|---|
| Date of isolation | December 22, 1966 | November 9, 1966 | November 9, 1966 |
| Method | pollen | pollen | pollen |
| Origin | Kenya, near Ruiru coffee plantation, pH 5.6 | Eschwege district, near Frankershausen "Hielocher", pH 7.7 | Arfurt, Oberlahn district, soil from sunny position on rock, pH 7.3 |
| Mycelium | 0.3–1 $\mu$ | 0.3–1.3 $\mu$, septate | 0.3–1.2 $\mu$ |
| Shape of Sporangia | bottle-shaped cylindrical, "money-pouch-shaped" |  | ± spherical with wrinkled surface, in part irregular |
| Size of Sporangia | 3–10 × 5–16 $\mu$ |  | 3.5–12 $\mu$ |
| Shape of Spores | small rods |  | ± spherical |
| Size of Spores | 0.5–0.7 × 1.5–2.2 $\mu$ |  | approx. 1–1.3 $\mu$ |
| Flagellation | lophotrichous |  | mobile spores |
| Arrangement of Spores in Sporangium | linear parallel chains |  | coiled-up chains |
| Conidia, Substrate spores and the like |  | on CPC broad hyphen (approx. 1.3 $\mu$), septate at intervals of approx. 2.5–4 $\mu$ optically dense, permanent cells? |  |
| Melanine | CPC +<br>Ty + | CPC −<br>Ty − +<br>Gel + − | CPC −<br>Ty − +<br>Gel + |
| Nitrate reduction |  | + | + |
| Gelatine liquefaction | − | + | + |
| Milk peptonization | − | + | + |
| Starch-hydrolysis |  |  |  |
| Growth at 20°C. | ++ | ++ | ++ |
| 26°C. | ++ | ++ | ++ |
| 32°C. | ++ | ++ | ++ |
| 37°C. | ++ | + | ++ |

Table 2-continued

|  | Ampullariella regularis SE 39 | Actinoplanes spec. SB 11 | Actinoplanes spec. SB 12 |
|---|---|---|---|
| 42°C. | — | — | — |

|  | Actinoplanes spec. SB 18 | Actinoplanes spec. SB 27 | Actinoplanes spec. SB 46 | Actinoplanes spec. SE 50 |
|---|---|---|---|---|
| Date of isolation | December 4, 1966 | December 8, 1966 | March 3, 1967 | December 22, 1969 |
| Method | pollen | pollen | pollen | pollen |
| Origin | Hattenheim, Rheingau, potato field in the "Sandaue", pH 8.0 | Kuhkoph, Nature Reserve, Altrhein, riverside wood, under willows, pH 7.6 | Neuhof, Fulda district, turf soil, edge of path, pH 6.1 | Kenya, near Ruiru coffee plantation, pH 6.2 |
| Mycleium | 0.3–1.3 $\mu$ septate | 0.2–1.1 $\mu$ | 0.3–1.4 $\mu$ septate | 0.4–1.3 $\mu$ |
| Shape of Sporangia | irregular, wrinkled, humped | ± club-shaped or oval to cylindrical, in part irregular, surface wrinkled | irregular, folded, humped | irregular, humped, wrinkled |
| Size of Sporangia | 6–16 $\mu$ | 4–16 $\mu$ | 6–20 $\mu$ | 4–13 $\mu$ |
| Shape of Spores | ± spherical, in part with nose-like protuberance | ± spherical | ± spherical | ± spherical |
| Size of Spores | 1–1.7 $\mu$ | 1–1.3 $\mu$ | approx. 1.2–2 $\mu$ | approx. 1 $\mu$ |
| Flagellation | bundles of flagellae | mobile spores | | |
| Arrangement of Spores in Sporangium | coiled chains | slightly coiled, in part parallel and straight chains | coiled chains, in part parallel | coiled chains, parallel in places |
| Conidia, Substrate spores and the like |  |  | on CPC substrate spores, up to 3 $\mu$ $\phi$, singly or intercalar to give several in a row |  |
| Melanine | CPC − <br> TY − <br> Gel +  } + | CPC − <br> Ty − <br> Gel − } − | CPC − <br> Ty − <br> Gel − } − | CPC + <br> Ty + } + |
| Nitrate reduction | − | + | + | − |
| Gelatine liquefaction | + | + | + | + |
| Milk peptonization | + | + | + | + |
| Starch-hydrolysis | + | | | |
| Growth at 20°C. | ++ | ++ | ++ | ++ |
| 26°C. | ++ | ++ | ++ | ++ |
| 32°C. | ++ | ++ | ++ | ++ |
| 37°C. | + | + | − | ++ |
| 42°C. | − | − | − | − |

|  | Actinoplanes spec. SA 8 | Actinoplanes spec. SE 82 | Actinoplanes spec. SE 103 |
|---|---|---|---|
| Date of isolation | June 26, 1966 | February 26, 1971 | March 2, 1971 |
| Method | pollen | pollen | pollen |
| Origin | Marburg, compost earth, botanic garden | Ceylon, earth, rubber plantation | Corsica, near Holy Trinity, from earth under cork-oaks |
| Mycelium | 0.3–1.3 $\mu$ | 0.3–1.3 $\mu$ |  |
| Shape of Sporangia | irregular | irregular | irregular |
| Size of Sporangia | 7–15 × 9–18 $\mu$ | 5–14 $\mu$ | about 5–13 $\mu$ |
| Shape of spores | ± spherical | ± spherical | ± spherical |
| Size of spores | about 1.5 $\mu$ | about 1–1.4 $\mu$ | about 1 $\mu$ |
| Flagellation | mobile |  | rapidly mobile |
| Arrangement of Spores in Sporangium | coiled chains | coiled chains |  |
| Melanine | Ty + <br> Gel 30 } + <br> CPC − |  |  |
| Nitrate reduction | + (very low) |  |  |
| Gelatine liquefaction | + |  |  |
| Milk peptonization | + |  |  |

|  | Streptosporangium roseum SS 55 | Streptosporangium amethystogenes roseum SS 59 | Streptosporangium SS 62 |
|---|---|---|---|
| Isolation date | November 10, 1968 | November 10, 1968 | November 10, 1968 |
| Method | soil smear, plate | soil smear, plate | soil smear, plate |
| Origin | Kenya, near Ruiru, earth from coffee field | Kenya, near Njoro, from field | Kenya, near Njoro, from field |
| Mycelium | 0.4–1.2 $\mu$ |  | 0.4–1.2 $\mu$ |
| Shape of sporangia | spherical | spherical | spherical |
| Size of sporangia | 3–10 $\mu$ | 3–15 $\mu$ | 3–10 $\mu$ |
| Shape of spores | mostly oval |  | mostly oval |
| Size of spores | about 0.8 × 1–1.2 $\mu$ |  | about 0.8–1.1 × 1–1.5 $\mu$ |
| Melanine | − | − | ++ |
| Nitrate reduction | ++ |  | ++ |
| Gelatine liquefaction | + |  | + |

Table 2-continued

|  | Streptosporangium roseum SS 55 | Streptosporangium amethystogenes roseum SS 59 | Streptosporangium SS 62 |
|---|---|---|---|
| Milk peptonization | + | + | + |
| Starch hydrolysis | + | + | + |
| Growth at 37°C. | + | + | + |
| 42°C. | − | − | − |
| NaCl 2% | | + | |
| toleration 3% | + | − | + |
| 4% | − | | − |

|  | Ampullariella digitata SA 28 | Ampullariella regularis SE 45 | Ampullariella spec. SE 89 |
|---|---|---|---|
| Isolation date | November 10, 1967 | December 23, 1969 | February 27, 1971 |
| Method | fungus mycelium | pollen | pollen |
| Origin | Amonau Krs. Marburg, earth from stubble-field | Kenya, near Ruiru, earth from coffee field | Ceylon, earth |
| Mycelium | 0.3–1 μ | | |
| Shape of sporangia | very narrow and relatively long, distally and in part also laterally irregular, in part fingered, coil-like or finger-shaped | bottle-shaped, cylindrical, often longitudinally narrow | ± cylindrical, frequently also broader than long, often not flat at the distal end, tubercular, in part also irregular and folded, a few fingered |
| Size of sporangia | 2–7 × 4–13 μ | 4–10 × 6–17 μ | 5–12 × 6–16 μ |
| Shape of sporangia | small rod-shaped | small rods | small rod-shaped |
| Arrangement of Spores in sporangia | arranged in parallel rows | in parallel straight rows | |
| Melanine | Ty −  <br> Gel −  + <br> CPC + | Ty + | |
| Nitrate reduction | + | | |
| Gelatine liquefaction | + | | |
| Milk peptonization | + | + | |

|  | Planomonospora spec. SE 100 | Planomonospora parontospora Se 101 | Pilimelia spec. SK 2 |
|---|---|---|---|
| Isolation date | March 1, 1971 | February 27, 1971 | January 28, 1968 |
| Method | pollen | pollen | pollen |
| Origin | Corsica, northern Algeria, earth, tree nursery | Ceylon, lawn earth | Marburg, garden earth, Schulerpark |
| Mycelium | | | 0.3–0.7 μ |
| Shape of sporangia | | longitudinally narrow, stand compactly by each other in parallel double rows in the air mycelium, arcuately bent air-hyphens on the convex side directly joined to their base | spherical, pear-shaped, oval, with a columella, which projects, as a continuation of the sporangiophor, up to about ⅓ of the sporangia —φ or further into the sporangium |
| Size of sporangia | | about 1–1.3 × 3–4.5 μ | about 7–15 μ |
| Shape of spores | | | small rods often slightly warped |
| Size of spores | | | 0.35–0.45 × 0.8–1.5 μ |
| Flagellation | | | mobile flagellar fascides |
| Arrangement of spores in sporangium | | | lateral (and also subpolar), spore arrangement in chains, which grow tuft-like from the columella |
| Melanine | | | Ty + |
| Nitrate reduction | | | + |
| Gelatine liquefaction | | | + |
| Milk peptonization | | | + |
| Growth at 32°C. | | | + |
| 37°C. | | | − |

Table 3

| G = growth <br> Spg = sporangium | | | SM = substrate mycelium <br> C = colony shape | | SP = soluble pigment <br> AM = aerial mycelium | |
|---|---|---|---|---|---|---|
| | | | SB 2 | | SB 5 | SB 11 |
| Casamino-peptone- | 1) | G. | very good | G. good | G. | good |
| | 2) | SM. | orange | SM. yellow-orange | SM. | beautiful orange, bleaching |
| Czapek agar | 3) | SP. | agar yellowish | SP. agar yellowish | SP. | agar yellowish |
| (CPC) | 4) | Spg. | +++; rimy | Spg. −; originally + | Spg. | − |
| | 5) | C. | flat and smooth | C. heavily veined | C. | with coiled ridges |
| | | G. | very good | G. good to very good | G. | good |
| Peptone- | | SM. | orange, rimy | SM. orange-red | SM. | orange, bleaching |

Table 3-continued

| | G = growth<br>Spg = sporangium | | SM = substrate mycelium<br>C = colony shape | | SP = soluble pigment<br>AM = aerial mycelium | |
|---|---|---|---|---|---|---|
| | | SB 2 | | SB 5 | | SB 11 |
| Czapek agar<br>(PC) | SP.<br>Spg.<br>C. | −<br>++<br>flat, in part humped | SP.<br>Spg. | agar yellowish<br>− | SP.<br>Spg. | agar golden yellow<br>− |
| Czapek agar<br>(Cz) | G.<br>SM.<br>SP. | moderate<br>orange<br>agar pale ochre | G.<br>SM.<br>SP. | moderate<br>pale orange<br>agar slightly yellowish | G.<br>SM.<br>SP. | good<br>brownish orange<br>− |
| Milk agar<br>(Ca) | Spg.<br>G.<br>SM.<br>SP.<br>Spg. | ++<br>good<br>brownish orange<br>agar brownish<br>−; casein peptonized | Spg.<br>G.<br>SM.<br>SP.<br>Spg. | −<br>very good<br>brownish orange<br>agar golden brown<br>−; casein peptonized | Spg.<br>G.<br>SM.<br>SP.<br>Spg. | −<br>very good<br>brownish orange, turns pale brown<br>agar yellow brown<br>−; casein peptonized |
| Tyrosine agar<br>(Ty) | G.<br>SM.<br>SP. | moderate-good<br>reddish brown<br>agar reddish brown, slight solution of crystals | G.<br>SM.<br>SP. | slight<br>brown<br>agar brown solution of crystals − | G.<br>SM.<br>SP. | bulky<br>pale orange<br>−<br>Tyrosine crystals not dissolved |
| Oat-Yeast agar<br>(OY) | Spg.<br>G.<br>SM.<br>SP.<br>Spg. | +; rimy<br>good<br>brownish orange<br>−<br>+++ | Spg.<br>G.<br>SM.<br>SP.<br>Spg. | −<br>good<br>brownish orange<br>−<br>+ | G.<br>SM.<br>SP.<br>Spg.<br>G.<br>SM. | good<br>ochre-orange<br>−<br>−<br>bulky<br>colorless to pale ochre |
| Starch agar | | | | | SP.<br>Spg. | −<br>− |

| | | SB 12 | | SB 18 | | SB 27 |
|---|---|---|---|---|---|---|
| Casamino-Peptone-<br>Czapek agar<br>(CPC) | G.<br>SM.<br>SP.<br>Spg.<br>C. | very good<br>orange-brown<br>agar yellowish-brownish<br>+<br>flat with radial grooves, bulging in the middle | G.<br>SM.<br>SP.<br>Spg.<br>C. | very good<br>strong red-brown<br>agar brown<br>+(+)<br>flat, radial grooves and wrinkles | G.<br>SM.<br>SP.<br>Spg.<br>C. | good to very good<br>luminous orange, later brown orange<br>agar yellow-brown<br>+<br>flat, bulging in the middle, locally split open |
| Peptone-Czapek agar<br>(PC) | G.<br>SM.<br>SP.<br>Spg.<br>G.<br>SM. | very good<br>brown red<br>agar golden brown<br>−<br>good<br>orange to brownish orange | G.<br>SM.<br>SP.<br>Spg.<br>G.<br>SM. | very good<br>brown<br>brown<br>++<br>good<br>red brown | G.<br>SM.<br>SP.<br>Spg.<br>G.<br>SM. | good to very good<br>ochre orange<br>agar yellowish<br>−<br>good<br>red brown |
| Czapek agar<br>(Cz) | SP.<br>Spg. | agar flouresces greenish to yellow<br>− | SP.<br>Spg. | agar reddish brown<br>++; rimy | SP.<br>Spg. | agar slightly ochre<br>− |
| Milk agar<br>(Ca) | G.<br>SM.<br>SP.<br>Spg. | very good<br>brown orange<br>agar golden brown<br>−; casein peptonized | G.<br>SM.<br>SP.<br>Spg. | very good<br>brown orange<br>agar golden brown<br>++, not always; casein peptonized | G.<br>SM.<br>SP.<br>Spg. | very good<br>brownish orange<br>agar golden brown<br>+, not always casein peptonized |
| Tyrosine agar<br>(Ty) | G.<br>SM.<br>SP. | moderate<br>brown<br>agar brown; crystal solution ++ | G.<br>SM.<br>SP. | moderate − good<br>reddish orange brown<br>agar orange brown; crystal solution ++ | G.<br>SM.<br>SP. | moderate − good<br>ochre brown<br>−<br>crystal solution ++ |
| Oat-Yeast agar<br>(OY) | Spg.<br>G.<br>SM.<br>SP.<br>Spg. | −<br>good<br>pale orange<br>−<br>+ | Spg.<br>G.<br>SM.<br>SP.<br>Spg. | −<br>good<br>red brown<br>red brown<br>++ | Spg.<br>G.<br>SM.<br>SP.<br>Spg. | −<br>good<br>orange brown<br>−<br>− |
| Starch-agar | G.<br>SM.<br>SP.<br>Spg. | bulky to good<br>pale brownish orange<br>−<br>+ | G.<br>SM.<br>SP.<br>Spg. | bulky to good<br>pale brownish orange<br>−<br>++ | G.<br>SM.<br>SP.<br>Spg. | bulky to good<br>pale brownish orange<br>−<br>++ |

| | | SB 46 | | SE 21 | | SE 39 | | SE 50 |
|---|---|---|---|---|---|---|---|---|
| Casamino-<br>peptone-<br>Czapek agar<br>(CPC) | G.<br>SM.<br>SP.<br>Spg.<br>C. | good<br>orange, later brownish orange<br>agar pale yellowish<br>+<br>flat, with radial grooves | G.<br>SM.<br>SP.<br>Spg. | good<br>orange brown<br>agar yellow brown<br>+; some | G.<br>SM.<br>SP.<br>Spg. | good<br>red brown<br>agar golden brown − red brown<br>++; rimy | G.<br>SM.<br>SP.<br>Spg. | very good<br>brown<br>agar brown to yellowish brown<br>− |
| Peptone-<br>Czapek agar | G.<br>SM.<br>SP. | good<br>orange<br>agar golden | G.<br>SM.<br>SP. | very good<br>dark brown<br>brown | G.<br>SM.<br>SP. | very good<br>reddish dark brown<br>dark brown | G.<br>SM.<br>SP. | very good<br>brown |

Table 3-continued

| | | SB 46 | | SE 21 | | SE 39 | | SE 50 |
|---|---|---|---|---|---|---|---|---|
| (PC) | Spg. | yellow — | Spg. | + | Spg. | ++ frost-like on the SM | | |
| | G. | good | G. | good | G. | good | G. | very good |
| | SM. | orange brown | SM. | orange | SM. | red-brown | SM. | red-brown |
| | SP. | agar ochre-colored | SP. | — to pale yellowish | SP. | red | SP. | gold brown |
| | Spg. | — | Spg. | +++ frost-like on the SM | Spg. | + | | |
| Milk agar | G. | very good | G. | good | G. | good | G. | good |
| | SM. | orange | SM. | brown-orange | SM. | brown-orange | SM. | orange brown |
| (Ca) | SP. | agar golden-colored | SP. | brown | SP. | dark brown | SP. | dark brown |
| | Spg. | —; casein peptonized | Spg. | — casein peptonized | Spg. | — casein not peptonized | Spg. | — casein peptonized |
| | G. | good | G. | bulky | G. | bulky | G. | bulky |
| Tyrosine agar | SM. | brown | SM. | dark brown | SM. | dark brown | SM. | dark, like the agar |
| (Ty) | SP. | agar golden brown; crystal solution ++ | SP. | dark brown | SP. | dark brown | SP. | black-brown |
| | Spg. | — | Spg. | — tyrosine crystals not dissolved | Spg. | — tyrosine crystals not dissolved | Spg. | — tyrosine crystals not dissolved |
| Oat-Yeast agar | G. | good | | | | | | |
| | SM. | orange brown | | | | | | |
| | SP. | — | | | | | | |
| (OY) | Spg. | — | Spg. | ++ | | | Spg. | + |
| "Emerson" agar E (yeast-starch agar) | | | | | | | G. | good |
| | | | | | | | SM. | brown |
| | | | | | | | SP. | brown |
| | | | | | Spg. | ++ | Spg. | — |
| Starch agar | | | G. | bulky to good | G. | bulky to good | G. | bulky to good |
| | | | SM. | pale brownish | SM. | pale brownish orange | SM. | pale brownish orange |
| | | | SP. | — | SP. | — | starch hydrolysis | — |
| | | | Spg. | + | Spg. | + | Spg. | + |

| | | | SE 5 | | SE 55 | | SE 103 |
|---|---|---|---|---|---|---|---|
| | | G. | good | G. | good | G. | good |
| | | SM. | orange | SM. | dark red brown | SM. | orange |
| Casamino-peptone-Czapek agar | | AM. | — | AM. | — | | |
| (CPC) | | SP. | — to pale yellowish | SP. | yellow brown | SP. | yellowish-brownish |
| | | | surface of colony in inclined test-tube shows slimy gloss | | | Spg. | — |
| Oat-Yeast agar | | G. | good | G. | good | G. | very good |
| | | SM. | orange | SM. | orange brown | SM. | brown |
| (OY) | | | | AM. | — | | |
| | | | | SP. | light brown | SP. | — |
| | | | | | | Spg. | ++, frost-like |
| | | G. | good | | | G. | very good |
| | | SM. | orange | | | SM. | orange |
| | | AM. | — | | | | |
| | | SP. | — | | | SP. | — |
| | | | surface of colony slimy | | | Spg. | ++, frost-like |
| Milk agar | | G. | good | G. | good | | |
| | | SM. | orange | SM. | orange brown | | |
| (Ca) | | SP. | — to yellowish | SP. | brown | | |
| | | | Casein not peptonized, except merely negligibly immediately around the mycelium | | Casein not peptonized, after about 2 months slightly peptonized | | |
| Czapek agar | | G. | good | G. | good | G. | very good |
| (Cz) | | SM. | orange, surface damp and shiny | SM. | orange | SM. | yellow-orange |
| | | SP. | — | SP. | — | SP. | — |
| | | | | | | Spg. | — |
| Tyrosine agar | | G. | small to bulky | G. | bulky | | |
| (Ty) | | SM. | colorless to pale orange | SM. | dark brown | | |
| | | SP. | — | SP. | black brown | | |
| | | | tyrosine crystals not dissolved | | tyrosine crystals not dissolved | | |
| Peptone-Czapek Agar (PC) | | | | G. | very good | | |
| | | | | SM. | dark reddish brown | | |
| | | | | SP. | dark brown | | |
| Starch agar | | | | G. | bulky to good | | |
| | | | | SM. | pale orange brown | | |
| | | | | SP. | — | | |
| | | | | Spg. | + | | |

| | | SS 45 | | SS 51 | | SS 53 |
|---|---|---|---|---|---|---|
| | G. | moderate (to good) | G. | moderate (to good) | G. | good |
| Casamino-peptone-Czapek agar | SM. | reddish brown | SM. | reddish brown | SM. | pale light brown |
| | AM. | — | AM. | — | AM. | white |
| | SP. | — | SP. | — | SP. | brownish |

Table 3-continued

|  |  | SS 45 |  | SS 51 |  | SS 53 |
|---|---|---|---|---|---|---|
| (CPC) |  | colony flat, 6 mm φ after 9 weeks |  | colony flat, 6 mm φ after 9 weeks |  | colony flat, center without AM |
|  | G. | good | G. | good | G. | good to very good |
| Oat-Yeast agar (OY) | SM. | brown red | SM. | brown red | SM. | purple brown to red brown |
|  | AM. | +, white and pink | AM. | +, white and pink | AM. | ++, dirty white and pink |
|  | SP. | pale yellowish to yellowish-greenish | SP. | pale yellowish with greenish tinge | SP. | purple-red brown |
|  | Spg. | + | Spg. | + | Spg. | ++ |
|  | G. | good | G. | good | G. | good |
| "Emerson" agar (E) | SM. | red | SM. | brown red | SM. | red brown |
|  | AM. | — | AM. | +, slight, white | AM. | ++, pink |
|  | SP. | pale yellowish with greenish tinge | SP. | — to pale yellowish brownish | SP. | red brown |
|  |  |  |  |  | Spg. | ++ |
|  | G. | good | G. | good | G. | good |
| Milk agar (Ca) | SM. | pale brownish red | SM. | pale brownish red | SM. | pale light brown |
|  | AM. | — | AM. | — | AM. | — |
|  | SP. | agar gold-yellow Casein peptonized | SP. | agar gold-yellow Casein peptonized | SP. | agar yellow brown Casein peptonized |
|  | G. | good | G. | good | G. | good |
| Yeast-glucose-soil extract agar (YGS) | SM. | brownish red | SM. | brown red | SM. | brownish claret |
|  | AM. | + thin coating | AM. | +, white | AM. | ++, pink |
|  | SP. | golden yellow with greenish tinge | SP. | yellow with greenish tinge | SP. | reddish yellow brown |
| Manure extract agar (Ma) | G. | moderate (to good) | G. | moderate (to good) |  |  |
|  | AM. | ++, white and pink | AM. | ++, pink |  |  |
|  | Spg. | + | Spg. | + |  |  |
|  |  | SA 8 |  | SE 82 |  | SS 26 |
|  | G. | very good | G. | good | G. | good |
| Casamino-peptone Czapek agar (CPC) | SM. | orange | SM. | brown | SM. | pale ochre |
|  |  |  |  |  | AM. | few, white |
|  | SP. | yellowish-brownish | SP. | brown | SP. | — |
|  | Spg. | + |  |  | Spg. | — |
|  |  |  |  |  |  | colony flat with a few radial grooves and concentric humps |
| Peptone Czapek agar (PC) | G. | very good |  |  |  |  |
|  | SM. | orange |  |  |  |  |
|  | SP. | yellowish-brownish |  |  |  |  |
|  | Spg. | + |  |  |  |  |
|  | G. | good | G. | very good | G. | good to bulky |
| Oat-Yeast agar (OY) | SM. | brown | SM. | orange to brownish orange | SM. | colorless |
|  |  |  |  |  | AM. | few, white |
|  | SP. | — | SP. | weak yellowish-brownish | SP. | — |
|  | Spg. | + |  |  | Spg. | + |
|  |  |  | G. | very good | G. | bulky |
| "Emerson" agar (E) |  |  | SM. | orange-brown | SM. | colorless |
|  |  |  |  |  | LM. | +, white |
|  |  |  | SP. | brown | SP. | — |
|  | G. | very good |  |  | G. | good |
| Milk agar (Ca) | SM. | orange brown |  |  | SM. | colorless |
|  | SP. | agar gold-brown |  |  | LM. | — |
|  | Spg. | + |  |  | SP. | — |
|  |  | Casein peptonized |  |  |  | Casein peptonized |
| Czapek agar (Cz) | G. | good | G. | good |  |  |
|  | SM. | brown-orange | SM. | red-orange |  |  |
|  | SP. | yellow brown | SP. | yellowish |  |  |
|  | Spg. | — |  |  |  |  |
| Tyrosine agar (Ty) | G. | bulky |  |  |  |  |
|  | SM. | black |  |  |  |  |
|  | SP. | black tyrosine crystals dissolved |  |  |  |  |
|  | Spg. | — |  |  |  |  |
| Yeast-glucose-soil extract agar (YGS) | G. | good |  |  | G. | good |
|  | SM. | brown |  |  | SM. | colorless |
|  | SP. | gold-brown |  |  | LM. | +, white |
|  | Spg. | + |  |  | SP. | — |
| Manure extract agar (Ma) |  |  |  |  | G. | bulky |
|  |  |  |  |  | SM. | pale brown |
|  |  |  |  |  | LM. | +, white |
|  |  |  |  |  | Spg. | + |
|  |  | SS 55 |  | SS 59 |  | SS 62 |
| Casamino-peptone-Czapek agar (CPC) | G. | good, colony flat |  |  | G. | good, colony flat |
|  | SM. | light brown |  |  | SM. | pale light brown |
|  | AM. | white |  |  | AM. | white |
|  | SP. | weak pale brown |  |  | SP. | — |
|  | G. | good | G. | good | G. | good |
|  | SM. | pale light brown | SM. | dark brown | SM. | pale light brown |
| Milk agar | AM. | — | AM. | — | AM. | — |
|  | SP. | — | SP. | yellow brown violet crystals Casein peptonized | SP. | agar yellow-brown Casein peptonized |
|  |  | Casein peptonized |  |  |  |  |
|  | G. | good | G. | good | G. | good |

Table 3-continued

| | | SS 55 | | SS 59 | | SS 62 |
|---|---|---|---|---|---|---|
| Tyrosine agar (Ty) | SM. | brown | SM. | dark brown | SM. | brown |
| | AM. | white | AM. | — | AM. | few, white |
| | SP. | — | SP. | brown | SP. | brown |
| | | tyrosine crystals dissolved | | tyrosine crystals dissolved | | tyrosine crystals dissolved |
| Oat-Yeast agar (OY) | G. | good to very good | G. | good | G. | good to very good |
| | SM. | red-brown | SM. | dark brown | SM. | red brown |
| | AM. | dirty pink | AM. | few, white | AM. | dirty pink |
| | SP. | red brown | SP. | brownish many violet crystals | SP. | red brown |
| | | | Spg. | — | | |
| "Emerson" agar (E) | G. | good | G. | good | G. | good |
| | SM. | red brown | SM. | dark brown | SM. | red brown |
| | AM. | pink and white | AM. | — | AM. | few, thin coating, in part stronger and pink |
| | SP. | red brown | SP. | yellow brown violet crystals | SP. | red brown |
| Yeast-glucose soil extract agar (YGS) | G. | good | G. | good | G. | good |
| | SM. | red brown | SM. | dark brown | SM. | dark red |
| | AM. | pink | AM. | — | AM. | pink |
| | SP. | yellow-brown | SP. | yellow brown violet crystals | SP. | yellow brown |

| | | SA 28 | | SE 45 | | SE 89 |
|---|---|---|---|---|---|---|
| Casamino peptone Czapek agar (CPC) | G. | good to very good | G. | good | G. | good |
| | SM. | initially red-brown, later dark brown to black | SM. | red-brown | SM. | brownish orange |
| | SP. | dark olive | SP. | strongly red-brown | SP. | — |
| | Spg. | — | Spg. | + | Spg. | + |
| Peptone Czapek agar (PC) | G. | good to very good | | | | |
| | SM. | initially red-brown, later dark brown to black | | | | |
| | SP. | dark olive | | | | |
| | Spg. | — | | | | |
| Czapek agar (Cz) | G. | bulky to good, colonies flat | G. | good | G. | good |
| | SM. | orange brown | SM. | brown-red | SM. | dark-brown |
| | SP. | weak ochre | SP. | brownish-red | SP. | light yellowish brown |
| | Spg. | +, in part frost-like | Spg. | ++, frost-like | Spg. | ++, frost-like |
| Milk agar (Ca) | G. | very good | G. | good | | |
| | SM. | black brown | SM. | orange brown | | |
| | SP. | dark olive to greenish-black | SP. | brown | | |
| | Spg. | — | Spg. | + | | |
| | | Casein peptonized | | Casein peptonized | | |
| Tyrosine agar (Ty) | G. | bulky to good | G. | bulky | | |
| | SM. | brown | SM. | brown | | |
| | SP. | — | SP. | dark brown | | |
| | Spg. | — | Spg. | — | | |
| | | tyrosine crystals dissolved under mycelium | | tyrosine crystals not dissolved | | |
| Oat-yeast agar (OY) | G. | good | G. | good | G. | good to very good |
| | SM. | dark brown | Spg. | ++, frost-like on the SM. | SM. | orange |
| | SP. | light brownish | | | SP. | — |
| | Spg. | + | | | Spg. | ++, frost-like |
| "Emerson" agar (E) | G. | good to very good | | | G. | very good |
| | SM. | brown to brown-black | | | SM. | orange |
| | SP. | ochre with greenish tint | | | SP. | — |
| | Spg. | + | | | Spg. | ++, frost-like |

| | | SE 100 | | SE 101 | | SK 2 |
|---|---|---|---|---|---|---|
| Casamino-peptone Czapek agar (CPC) | G. | good | G. | good | | |
| | SM. | pale ochre | SM. | red | | |
| | AM. | ++, white | AM. | few, white | | |
| | SP. | — | SP. | — | | |
| Czapek agar (Cz) | G. | good | G. | bulky | | |
| | SM. | colorless | SM. | colorless to pink | | |
| | AM. | ++, white | AM. | +, white | | |
| | SP. | — | | | | |
| "Emerson" agar (E) | G. | good | G. | good | | |
| | SM. | colorless to pale ochre | SM. | pale red to red, later paling | | |
| | AM. | ++, white | AM. | — | | |
| | SP. | — | SP. | — | | |
| Oat-yeast agar (OY) | G. | good | G. | good | G. | bulky |
| | SM. | pale ochre | SM. | pink | SM. | brown |
| | AM. | ++, white | AM. | ++, dirty pink | SP. | — |
| | SP. | — | SP. | yellowish-brownish | | |
| | | | Spg. | ++ | | |
| Milk agar (Ca Ca/2) | | | | | G. | good (relatively) |
| | | | | | SM. | golden yellow surface knobby |
| | | | | | SP. | — |
| | | | | | Spg. | — |
| | | | | | | Casein peptonized |

Table 3-continued

|  | SE 100 | SE 101 | SK 2 |
|---|---|---|---|
| Tyrosine agar (Ty) | | | G. good<br>SM. brownish gold-yellow to yellow-orange<br>SP. golden brown to reddish brown<br>Spg. —<br>tyrosine crystals dissolved |

Table 4

Growth in Various Carbon Sources

|  | SB2 | SB5 | SB11 | SB12 | SB18 | SB25 | SB46 | SE21 | SE39 | SE50 | SE55 |
|---|---|---|---|---|---|---|---|---|---|---|---|
| Glucose | ++ | ++ | ++ | ++ | ++ | ++ | ++ | ++ |  | ++ | ++ |
| Fructose | ++ |  | ++ | ++ | ++ | ++ | ++ | ++ | ++ | ++ | ++ |
| Saccharose | ++ | ++ | ++ | ++ | ++ | ++ | ++ | ++ |  | ++ | ++ |
| Mannitol | ++ | ++ | ++ | ++ | ++ | ++ | ++ | − |  | ++ | ++ |
| L-Arabinase | ++ | ++ | ++ | ++ | ++ | ++ | ++ | ++ |  | ++ | ++ |
| Raffinose | − | − | ++ | − | − | − | − | − |  | + | + |
| Inositol | − | − | ++ | − | ++ | ++ | ++ | − |  | − | − |
| D-Xylose | ++ | ++ | ++ | ++ | ++ | ++ | ++ | ++ | ++ | ++ | ++ |

++ Growth as good as on glucose or better
+ Growth worse than on glucose, but better than on sugar-free mineral salt-agar
− Growth as on mineral salt-agar without carbon source The strains set forth in Table 1 were either drawn from established culture collections such as the American Type Culture Collection and the Centraalbureau voor Schimmelcultures, or deposited under the CBS-numbers set forth above in the Centraalbureau voor Schimmelcultures in Baarn, Holland.

Tables 2 and 3 list some characteristics of the strains described.

To obtain the glycoside-hydrolase inhibitors, the strains listed above are cultured in the nutrient solutions described above. In doing so it should be noted that for optimum production practically every strain requires a different nutrient solution of different qualitative and quantitative composition.

After 1 to 10 days' incubation at 15°–60°C., preferably 24°–50°C., in a shaking flask or in fermenters of different size, the mycelium is separated from the culture solution and, depending on the occurrence of the inhibitors, the active principle is concentrated using the culture solution and/or the mycelium.

The inhibitors are obtained from the culture broths by lyophilization or precipitation with salt or water-soluble organic solvents (such as, for example, lower alcohols and ketones) or by adsorption of the active substances on ion exchangers.

The inhibitors are obtained from the mycelia by extraction with organic solvents, such as, for example, alcohols, ketones, ethers, esters and sulphoxides.

For this purpose, the fermentation batch is centrifuged at 3,000–20,000 revolutions per minute, preferably 6,000–10,000 revolutions per minute, for 10–60 minutes, preferably 30 minutes, or is filtered, preferably under pressure and with the help of filter aids, such as, for example, Claricel, and is thus separated into culture broth and mycelium residue.

The inhibitor can be isolated from the particular culture broth in various ways:

a. Concentration of the culture broths under reduced pressure (10–50 mm Hg) at bath temperatures of 20°–100°C., preferably 40°–80°C., to approximately one-fifth to one-fiftieth of the initial volume. The concentrated extract is filtered or centrifuged and the clear filtrate (or the clear supernatant liquid is lyophilized, if required after prior desalination.

b. Precipitation of the inhibitors from the culture broth [or from the culture broths concentrated according to (a)] by adding water-soluble organic solvents, such as, for example, alcohols or ketones, preferably methanol, ethanol, or acetone, up to a content of 60–90%. Since inactive concomitant substances are precipitated at low concentration of solvents, this precipitation process is particularly suitable for fractional precipitation to remove undesired concomitant substances.

c. Salting-out of the inhibitors from the extracts [or from the extracts concentrated according to (a)], for example, with ammonium sulphate, sodium chloride and the like. The precipitate formed is collected by centrifuging or filtering and is either directly washed with acetone and ether and dried in vacuo or redissolved in water, dialyzed and lyophilized.

d. Adsorption of the inhibitors on ion exchangers. This process is suitable for isolating those inhibitors which, because of their chemical nature, carry a charge. The inhibitor is desorbed by changing the ionic strength or the pH value of the elution medium.

In addition to the inhibitor, undesired concomitant substances are frequently present in the culture broths. These concomitant substances can be separated off in various ways, for example, by denaturing the concomitant substances by means of heat in the case of inhibitors which are heat-stable, or by dialysis through appropriate membranes in the case of low molecular inhibitors, in which case the undesired concomitant substances are retained by the membrane, or by fractional precipitation [compare (b)] or by adsorption of the concomitant substances on ion exchangers.

The inhibitors are obtained from the mycelia by repeated extraction of the mycelium with organic solvents, preferably two extractions of 10–20 minutes with 3—5 volumes of acetone (relative to the moist mycelium volume) and subsequent single extraction of 5–10 minutes with ether. The mycelium extracted in this way is dried in vacuo and subsequently extracted for 2–8 hours with 3–10 parts by weight of dimethyl sulphoxide, while stirring, and thereafter centrifuged at 10,000 to 20,000 revolutions per minute. The acetone extracts and ether extracts are concentrated to dryness in vacuo and taken up with the dimethyl sulfoxide (DMSO) extract.

Instead of extracting the dry mycelium powder with dimethyl sulfoxide (DMSO), it can also be extracted over a longer period, preferably 12–24 hours, with water or dilute electrolyte solutions.

The new substances dissolve well in water. One group of the inhibitors is heat-stable at neutral pH values, stable to acid (pH 2), stable to alkali (pH 12), and slowly dialyzable These inhibitors are not inactivated by trypsin and pepsin and, in turn, do not inhibit the enzymes mentioned. They cannot be dyed with the typical protein dyes and do not show a characteristic absorption in the UV up to 250 nm. These inhibitors cannot be inactivated with urea and β-mercaptoethanol. According to estimates from gel filtration, the molecular weight of these inhibitors is above 500 but below 6,000. In hydrolytic splitting, monosaccharides, for example, glucose, are obtained. According to these findings, these inhibitors are oliogosaccharides or polysaccharides or their derivatives.

The best inhibitors of this group show inhibition activities, against amylase, of 8,000 AIU/mg.

Another group of inhibitors is heat-labile and not dialyzable, or hardly dialyzable. These inhibitors are inactivated more or less rapidly by trypsin. Urea and α-mercaptoethanol also inactivate most of these inhibitors. These inhibitors are probably substances of peptide character.

The best inhibitors of this group show inhibiting activities, against amylase, of 80 AIU/mg.

It is known that in the case of animals and man hyperglycemias arise after the intake of foodstuffs and beverages containing carbohydrates (for example, corn starch, potato starch, fruit, fruit juice or chocolate), these hyperglycemias resulting from a rapid degradation of the carbohydrates by glycoside-hydrolases (for example, salivary and pancreatic amylases, maltases and saccharases) in accordance with the following equation:

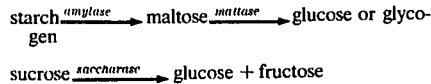

These hyperglycaemias are of particularly strong and lasting character in the case of diabetics. In adipose cases, alimentary hyperglycemia frequently causes a particularly strong secretion of insulin, which, in turn, leads to increased synthesis of fat and reduced degradation of fat. In connection with such hyperglycemias, a hypoglycemia frequently occurs in metabolically healthy and adipose persons as a result of the insulin secretion. It is known that not only hypoglycemias but also chyne remaining in the stomach stimulate the production of gastric juice, which for its part participates or encourages the formation of a gastritis, or a gastric or duodenal ulcer.

It has now been found that inhibitors of glycosidenhydrolases, according to the invention, obtained and isolated in accordance with the above methods, considerably reduces alimentary hyperglycemia, hyperinsulinemia and hypoglycemia after dosing rats and/or man with wheat starch or sucrose or maltose, and speed up the passage of these carbohydrates through the stomach.

Furthermore, it is known that carbohydrates, especially sucrose, are split by microorganisms in the mouth cavity and that caries formation is promoted thereby.

Inhibitors of glycoside-hydrolases are, therefore, suitable for use as therapeutic agents for the following indications: obesity, adiposit, hyperlipoidemia (arteriosclerosis) diabetes, pre-diabetes, gastritis, gastric ulcer, duodenal ulcer, and caries.

The present invention, therefore, provides a pharmaceutical composition containing as active ingredient an inhibitor of the invention in admixture with a liquid diluent other than a solvent of a molecular weight less than 200 (preferably less than 350) except in the presence of a surface active agent.

The invention further provides a pharmaceutical composition containing as active ingredient an inhibitor of the invention in the form of a sterile or isotonic aqueous solution.

The invention also provides a medicament in dosage unit form comprising an inhibitor of the invention either alone or in a admixture with a diluent.

The invention also provides a medicament in the form of tablets, (including lozenges and granules), dragees, capsules, pills, ampoules and suppositories comprising an inhibitor of the invention either alone or in admixture with a diluent.

"Medicament" as used in this specification means physically discrete coherent portions suitable for medical administration. "Medicament in dosage unit form" as used in this specification, means physically discrete coherent portions suitable for medical administration each containing a unit dose or a multiple (up to 4 times) or submultiple [down to a fortieth] of a unit dose of the inhibitor of the invention. Whether the medicament contains a unit dose or, for example, a half, a third, or a quarter of a unit dose will depend on whether the medicament is to be administered once, for example, twice, 3 times or 4 times a day, respectively.

A unit dose is the amount of inhibitor to be taken on one occasion.

The pharmaceutical compositions according to the invention may, for example, take the form of gels, pastes (e.g., toothpastes), creams, chewing-gums, suspensions, solutions and emulsions of the active ingredient in aqueous or non-aqueous diluents, syrups, granules or powders.

The diluents to be used in pharmaceutical composition (e.g., granulates) adapted to be formed into tablets, dragees, capsules and pills include the following: (a) fillers and extenders, e.g., starch, sugars, mannitol, and silicic acid; (b) binding agents, e.g., carboxymethyl cellulose and other cellulose derivatives, alginates, gelatine, and polyvinyl pyrrolidone; (c) moisturizing agents, e.g., glycerol; (d) disintegrating agents, e.g., agar-agar, calcium carbonate, and sodium bicarbonate, (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium, and magnesium stearate, and solid polyethylene glycols; (j) elastomeric binders such as chicle.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats [e.g., cocoa oil and high esters (e.g., $C_{14}$-alcohol and $C_{16}$-fatty acid)] or mixtures of these diluents.

The pharmaceutical compositions which are pastes, creams, and gels can, for example, contain the usual diluents, e.g., animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders can, for example, contain the usual diluents, e.g., lactose, talc, silicic acid, aluminum hydroxide, calcium silicate, and polyamide power or mixtures of these substances.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g., peppermint oil and eucalyptus oil) and sweetening agents (e.g., saccharin). In particular, chewing gums and toothpastes will contain flavoring agents.

The pharmaceutical compositions according to the invention preferably contain about 0.1 to 99.5, more preferably from about 0.5 to 95% of the inhibitor by weight of the total composition.

In addition to an inhibitor of the invention, the pharmaceutical compositions according to the invention can also contain other pharmaceutically active compounds. They may also contain a plurality of different inhibitors of the invention. Particular examples of such other pharmaceutically active compounds are oral antidiabetic agents such as $\beta$-cytotropic sulphonyl-urea derivatives and biguanides which influence the blood sugar level.

The diluent in the medicament of the present invention may be any of these mentioned above in relation to the pharmaceutical compositions of the present invention. Such medicament may include solvents of molecular weight less than 200 as sole diluent.

The discrete coherent portions constituting the medicament according to the invention (whether in dosage unit form or net) may be, for example, any of the following: tablets (including lozenges and granules), pills, dragees, capsules, suppositories, and ampoules. Some of these forms may be made up for delayed release of the inhibitor. Some, such as capsules, include a protective envelope which renders the portions of the medicament physically discrete and coherent.

The preferred unit dose for the medicaments of the invention is 5,000–500,000 AIU, 2.5–250 MIU, or 100–10,000 SIU of inhibitor. A unit dose will be taken orally once or several times daily, usually immediately before, during, or after a meal.

It is envisaged that the inhibitor will be administered perorally. Preferred medicaments are, therefore, those adapted for peroral administration, such as tablets, dragees, and portions of chewing gum.

The toxicity of some of these inhibitors of glycoside-hydrolases is extremely low. The active substance from Examples 14 and 37 was tolerated, without symptoms, at a dosage of $5 \times 10^6$ AIU/kg of mouse or rat, administered orally. In the case of intravenous injection, mice and rats tolerated $10^6$ AIU/kg.

The following examples illustrate the production of the inhibitor according to the invention.

EXAMPLE 1

Three 1-liter Erlenmeyer flasks, containing 200 ml of a nutrient solution of composition: 2% starch, 1% glucose, 0.5% NZ-amines, 1.0% yeast extract and 0.4% $CaCO_3$ (sterilization: 30 minutes, 121°C.; pH adjusted to 7.2 before sterilization) are each inoculated with 1 ml of a primary culture (obtained in the same nutrient solution, inoculated from sloping test-tube cultures with oatmeal agar) of the strain SB 2, and the flasks are incubated at 28°C. on a rotary shaking machine. After a period of culture of 5.5 days, the contents of the three flasks are combined and the mycelium is separated off by centrifuging. 425 ml of supernatant liquor, containing 100 AIU/ml, are obtained.

The centrifuged supernatant liquor is concentrated to 60 ml on a rotary evaporator at 15–20 mm Hg and approximately 37°C. waterbath temperature. The viscous solution is stirred into 8 volumes = 480 ml of ethanol, while stirring. The precipitate formed is collected by centrifuging, again dissolved in 60 ml of water, and dialyzed for 6 hours against distilled water. The dialyzate in lyophilized. Yield: 1.6 g containing $19 \times 10^3$ AIU/g.

EXAMPLE 2

Using a batch according to Example 1, 440 ml of centrifuged supernatant liquor containing 100 AIU/ml are obtained.

These 440 ml of centrifuged supernatant liquor are concentrated to 100 ml on a rotary evaporator. The concentrated solution is stirred into 8 volumes = 800 ml of ethanol and the precipitate is collected by centrifuging, twice washed with acetone and once with ether and dried in vacuo at room temperature. Yield: 2.2 g containing $15 \times 10^3$ AIU/g.

EXAMPLE 3

Using a batch according to Example 1, 500 ml of a centrifuged supernatant liquor containing 120 AIU/ml are obtained after 5 days' culture. These 500 ml are lyophilized directly. Yield: 7.1 g containing $8.3 \times 10^3$ AIU/g.

EXAMPLE 4

Three 1-liter Erlenmeyer flasks containing 200 ml of a nutrient solution of composition: 3% glycerine, 3% soya flour, and 0.2% $CaCO_3$ (sterilization: 30 minutes, 121°C.; pH after sterilization 7.2) are each inoculated with 1 ml of a primary culture (obtained in the same nutrient solution, inoculated from sloping test-tube cultures containing Czapek-peptone-casein agar) of the strain SB 12, and the flasks are incubated for 3 days at 28°C. on a rotary shaking machine. After the incubation, the contents of the flasks are combined and the mycelium is separated off by centrifuging. 500 ml of supernatant liquor containing 450 AIU/ml are obtained.

The supernatant liquor is treated with 250 g of ammonium sulphate added in portions while stirring and the mixture is subsequently centrifuged for 10 minutes at 12,000 revolutions per minute. The precipitate is dissolved in 100 ml of distilled $H_2O$ and 4 volumes (=400 ml) of acetone are added while stirring. A precipitate which sediments well is formed. The liquid is decanted off and the precipitate is washed twice with acetone and once with ether and dried in vacuo. Yield: 13.4 g containing $10 \times 10^3$ AIU/g.

EXAMPLE 5

A precipitate obtained according to Example 4 after precipitation with ammonium sulphate is dissolved in 100 ml of water and dialyzed for 6 hours against distilled water. A dialyzate is obtained, which is frozen and lyophilized. Yield: 1.5 g containing 80 AIU/mg.

EXAMPLE 6

If a 1 liter Erlenmeyer flask is inoculated with 120 ml of a nutrient solution according to Example 1, from a sloping test-tube culture of the strain St. 19, a culture solution containing 25 AIU/ml is obtained after 3 days' culture at 28°C. on a rotary shaking machine.

EXAMPLE 7

If a mix according to Example 4 is incubated for 3 days at 32°C., a culture filtrate containing 350 AIU/ml is obtained after filtering off the mycelium.

EXAMPLE 8

If a nutrient solution according to Example 1 is inoculated in accordance with Example 4, culture filtrates containing 270 AIU/ml are obtained after 3 days' incubation at 28°C.

EXAMPLE 9

Six 1-liter Erlenmeyer flasks, each containing 100 ml of a nutrient solution consisting of 3% glucose, 3% soya flour, and 0.2% $CaCO_3$ (sterilization: 30 minutes, 121°C.; pH after sterilization 7.2) are each inoculated with 1 ml of primary culture (obtained as in Example 1) of the strain SB 5, and are incubated for four days at 28°C. on rotary shaking machines. The contents of the flasks are combined and the mycelium is separated off by centrifuging. The resulting 500 ml of supernatant liquor containing 150 AIU//ml are frozen and lyophilized. Yield: 6.9 g containing $11 \times 10^3$ AIU/g.

EXAMPLE 10

If 24 flasks of a mix according to Example 4, each containing 120 ml, are inoculated with a primary culture of the strain SB 11 (obtained according to Example 4) and incubated for 5 days at 28°C., 2.0 liters of a supernatant liquor containing 1.1 MIU/ml are obtained after centrifuging. These 2 liters are concentrated to 200 ml on a rotary evaporator. The 200 ml of concentrate are dialyzed for 24 hours in a Visking dialysis tube (type 27/100 FT, Union Carbide Corporation) against 2 liters of distilled water, at room temperature. The outer medium, containing inhibitor, is concentrated to 100 ml on a rotary evaporator and is added dropwise to 900 ml of absolute ethanol, while stirring. The almost inactive precipitate which separates is centrifuged off and discarded, and the alcoholic supernatant liquor is concentrated to 30 ml on a rotary evaporator.

1 ml of this concentrate contains 70 MIU/ml.

For further purification, this solution is passed over an anion exchage column (Amberlite IRA 410, acetate form, in 0.05 M $NH_4$-acetate, pH 7, $2.5 \times 20$ cm column) and the active fractions are combined and gel-filtered on Sephadex $^R$ G 75 in $H_2O$. The active fractions from the gel filtration are concentrated to 12 ml. 1 ml of this solution contains 150 MIU/ml.

The mycelium (~500 ml) was twice extracted with 1 liter of acetone and once with 1 liter of ether and the extracts were combined and evaporated to dryness on a rotary evaporator in vacuo. The mycelium residue was dried in vacuo at 20°C. and the resulting dry mycelium powder (~51 g) was subsequently extracted for 2 hours at room temperature with 150 ml of dimethyl sulfoxide (DMSO). After centrifuging (30 minutes, 15,000 r.p.m.) the acetone/ether extract which has been concentrated to dryness is taken up with the dimethyl sulfoxide (DMSO) supernatant liquor from the dry mycelium powder. Yield: 120 ml containing 3 MIU/ml.

EXAMPLE 11

If a 1 liter Erlenmeyer flask containing 120 ml of a nutrient solution according to Example 1 is inoculated according to Example 9 and incubated for 6 days at 28°C. on a rotary shaking machine, a culture filtrate containing 0.9 MIU/ml is obtained.

EXAMPLE 12

If five 1-liter Erlenmeyer flasks, each containing 120 ml of a nutrient solution of composition: 2.5% starch, 0.5% glucose, 0.5% NZ-amines, 1.0% yeast extract and 0.4% $CaCO_3$ (sterilization: 30 minutes, 121°C.; pH adjusted to 7.2 before sterilization) are each inoculated with 2 ml of a primary culture (obtained according to Example 1) of the strain SB 27 and these flasks are incubated for 4 days at 28°C. on a rotary shaking machine, 500 ml of supernatant liquor containing 70 AIU/ml are obtained after combining the flasks and centrifuging off the mycelium. The centrifuged supernatant liquor is frozen and lyophilized. Yield: 7.7 g containing $3.5 \times 10^3$ AIU/g.

EXAMPLE 13

If a mix according to Example 1 is inoculated with 2 ml of a primary culture of the strain SB 18 (obtained according to Example 1) and incubated for 3 days at 28°C., a culture broth containing 1100 AIU/ml, 0.17 MIU/ml and 1.0 SIU/ml is obtained.

EXAMPLE 14

If five experimental fermenters each containing 8 liters of culture solution according to Example 1 are each inoculated with 120 ml of a primary culture (obtained according to Example 1) and incubated for 65 hours at 28°C. while stirring and aerating, 30 liters of culture broth are obtained after combining the fermentation broths and separating off the mycelium. These 30 liters of centrifuged culture broth (0.57 MIU/ml, 6.2 SIU/ml, and 8,000 AIU/ml) are concentrated to 5 liters in vacuo at 20 mm Hg and 100°C. bath temperature, 4 volumes (=20 liters) of acetone are added to the concentrate while stirring, and the black smeary precipitate which forms is collected by centrifuging at 6,000 r.p.m. for 30 minutes; the precipitate is dissolved in 2.5 liters of water and the black-colored solution is stirred for 60 minutes with 500 g of moist Amberlite [IRA 410 (acetate form, pH 7)]. The mixture is separated into supernatant liquor and Amberlite sediment by centrifuging for 10 minutes at 6,000 r.p.m. In the same way, the supernatant liquor is further stirred 3 times, in each case with 500 g of Amberlite for 60 minutes, and subsequently with a further 500 g of Amberlite overnight (~15 hours). After this treatment, the supernatant liquor shows a light yellow coloration, while the black concomitant dyestuffs were bonded to the ion exchanger. The collected Amberlite residues are twice washed with 1.5 liters of water and these wash waters are combined with the supernatant liquor containing inhibitor. The supernatant liquor, combined with the wash water, is concentrated to 1 liter in a rotary evaporator at 15 mm Hg and 80°C. bath temperature and subsequently added dropwise to 10 liters of acetone, with vigorous stirring. Hereupon, a white flocculent precipitate results, which is filtered off, washed with acetone and ether and dried in vacuo. Yield: 150 g of a white powder containing $1 \times 10^6$ AIU/g and 450 SIU/g.

EXAMPLE 15

If, in a nutrient solution according to Example 1, the glucose is replaced by other sugars or sugar alcohols and shaking flasks each containing 120 ml of culture solution are each inoculated with 1 ml of a primary culture of the strain SB 18 (manufactured according to Example 1), culture solutions containing the following amylase inhibitor concentrations are obtained after 3 or 4 days' culture at 28°C. on rotary shaking machines:

| Additive 1% Each | AIU/ml after 3 days | AIU/ml after 4 days |
|---|---|---|
| sucrose | 5,400 | 10,500 |
| lactose | 9,100 | 4,600 |
| maltose | 7,500 | 13,600 |
| galactose | 9,100 | 10,200 |
| glucose | 7,000 | 9,700 |
| sorbitol | 2,600 | 10,200 |
| mannitol | 8,500 | 8,700 |
| inositol | 4,800 | 5,600 |
| starch | 6,400 | 10,200 |

EXAMPLE 16

If a nutrient solution consisting of 3% soya flour, 2% starch, 1% glucose, and 0.2% $CaCO_3$ is inoculated and incubated in accordance with Example 15, a culture broth containing 5,600 AIU/ml is obtained after 4 days' fermentation.

EXAMPLE 17

If a mix according to Example 13 is inoculated and incubated with a morphological variant of SB 18, the strain SB 18/5, a culture broth containing 27,400 AIU/ml is obtained after 4 days' fermentation.

The strain SB 18/5 was deposited at the Central Bureau voor Schimmelcultures in Baarn, Holland, under CBS No. 613.71.

EXAMPLE 18

If a mix according to Example 13 in inoculated and incubated with a morphological variant of SB 18, the strain SB 18/4, a culture broth containing 13,900 AIU/ml is obtained after 4 days' fermentation.

The strain SB 18/4 was deposited at the Central Bureau voor Schmmelcultures in Baarn, Holland, under CBS No. 612.71.

EXAMPLE 19

If a nutrient solution of composition: 2% starch, 1% glucose, 0.3% glycine, 0.25% corn-steep liquor, 0.4% soya flour, 0.1% NaCl, 0.1% $K_2HPO_4$, 0.01% $FeSO_4$, and 0.01% $CaCO_3$ is inoculated and incubated in accordance with Example 12, a culture broth containing 2,900 AIU/ml is obtained after 3 days' incubation.

EXAMPLE 20

If two flasks of a mix according to Example 1 are inoculated with 1 ml of a primary culture of the strain SB 46 and incubated for 4 days at 28°C. on a rotary shaking machine, 250 ml of supernatant liquor containing 250 AIU/ml are obtained after centrifuging.

These 250 ml of supernatant liquor are treated with 150 g of ammonium-sulphate added in portions while stirring and the mixture is subsequently centrifuged for 15 minutes at 10,000 r.p.m. The residue is dissolved in 12 ml of $H_2O$ and dialyzed for 3 hours against distilled water. The 20 ml of dialysate are precipitated with 6 volumes (= 120 ml) of acetone in an ice bath and the precipitate is filtered off, washed with acetone and ether and subsequently dried in vacuo. Yield: 0.28 g containing $220 \times 10^3$ AIU/g.

EXAMPLE 21

If a 1 liter Erlenmeyer flask containing 120 ml of a nutrient solution according to Example 1 is inoculated with 2 ml of a primary culture of the strain SE 5 (produced according to Example 4) and incubated for 7 days on a rotary shaking machine at 28°C., a culture broth containing 0.09 MIU/ml is obtained.

The mycelium is treated with 50 ml of acetone, homogenized for one minute on an Ultraturrax homogenizer (Messrs. Janke and Kunkel, Staufen, Breisgau) and the mixture is subsequently centrifuged for 10 minutes at 3,000 r.p.m. The residue is again extracted, in the same way, with 50 ml of acetone and subsequently extracted once with 50 ml of ether, and the three extracts are combined and concentrated almost to dryness in a rotary evaporator at approximately 10–20 mm Hg and a waterbath temperature of 37°C.

The mycelium residue is dried in vacuo and subsequently treated with 15 ml of dimethyl sulphoxide (DMSO), homogenized for two minutes by means of the Ultraturrax and extracted for 2 hours while stirring (magnetic stirrer). Thereafter the mixture is centrifuged for 30 minutes at 20,000 r.p.m. The dimethyl sulfoxide (DMSO) extract is then decanted from the extracted mycelium, added to the residue of the acetone/ether extraction, and the mixture stirred for approximately 30 minutes (magnetic stirrer), and again centrifuged for 10 minutes at 20,000 r.p.m., and the clear supernatant liquor is tested as mycelium extract. 0.14 MIU/ml.

EXAMPLE 22

If two shaking flasks according to Example 1, each containing a charge of 160 ml, are each inoculated and incubated with 1 ml of a primary culture (according to Example 1) of the strain SE 21, 200 ml of a supernatant liquor containing 360 AIU/ml are obtained after centrifuging.

The centrifuged supernatant liquor is treated with 100 g of ammonium-sulphate added in portions while stirring and is centrifuged, the precipitate is dissolved in 20 ml of water and the solution is precipitated with 2 volumes (ca 40 ml) of acetone. The precipitate is washed with acetone and ether and dried in vacuo. Yield: 2 g containing $25 \times 10^3$ AIU/g.

EXAMPLE 23

If a mix according to Example 14 is inoculated and incubated with primary cultures of the strain SE 21, culture broths containing 140 AIU/ml are obtained after 65 hours' fermentation.

EXAMPLE 24

If a 1 liter Erlenmeyer flask containing 120 ml of a nutrient solution of the composition according to Example 4 is inoculated with 1 ml of a primary culture, according to Example 1, of the strain SE 39 and incubated in accordance with Example 1, a culture solution containing 50 AIU/ml is obtained after only 3 days' fermentation.

EXAMPLE 25

If glycerine is replaced by glucose in a mix according to Example 24, culture solutions containing 60 AIU/ml are obtained after 3 days.

EXAMPLE 26

If in a mix according to Example 24 the nutrient solution according to Example 1 is modified and the starch replaced by glucose, culture solutions containing 140 AIU/ml are obtained after 3 days' incubation.

EXAMPLE 27

If five 1-liter Erlenmeyer flasks each containing 120 ml of nutrient solution of composition: 3% glucose, 0.5% NZ-amines, 1.0% yeast extract and 0.4% $CaCO_3$ (sterilization: 30 minutes, 121°C.; pH before sterilization 7.2) are inoculated with 1 ml of a primary culture of the strain SE 39 (manufactured according to Example 4) and incubated for 3 days on a rotary shaking machine at 28°C., 500 ml of a supernatant liquor containing 160 AIU/ml are obtained after centrifuging.

The 500 ml of the supernatant liquor are precipitated with 6 volumes (= 3 liters) of acetone while stirring and the light brown precipitate is filtered off, washed with acetone and ether and dried in vacuo. Yield: 3.5 g containing $13.5 \times 10^3$ AIU/g.

EXAMPLE 28

If an Erlenmeyer flask containing 120 ml of a nutrient solution according to Example 4 is inoculated with 1 ml of a primary culture of the strain SE 50 (primary culture manufactured according to Example 4) and incubated, again in accordance with Example 4, a culture solution containing 1.0 SIU/ml is obtained after 5 days.

EXAMPLE 29

If Example 28 is followed but with a nutrient solution according to Example 1, a culture solution containing 26,000 AIU/ml and 0.18 MIU/ml and 1.8 SIU/ml is obtained after 5 days' incubation.

EXAMPLE 30

If Example 29 is followed but with a flask charge of 200 ml, a culture solution containing 24,500 AIU/ml and 0.18 MIU/ml and 2.1 SIU/ml is obtained after 5 days' incubation.

EXAMPLE 31

If Example 28 is followed, but with a nutrient solution of composition: 2% starch, 1% glucose, 0.3% glycine, 0.25% cornsteep liquor, 0.4% soya flour, 0.1% NaCl, 0.1% $K_2HPO_4$, 0.01% $MgSO_4$, 0.01% $CaCO_3$ and 0.01% $FeSO_4$, a culture solution containing 12,900 AIU/ml is obtained after 5 days' fermentation.

EXAMPLE 32

If, in a nutrient solution according to Example 1, the glucose is replaced by other sugars or sugar alcohols and the solution inoculated and incubated in accordance with Example 28, culture solutions containing the following amylase inhibitor concentrations are obtained:

| Additives (1%) | AIU/ml after 3 days | AIU/ml after 5 days |
| --- | --- | --- |
| sucrose | — | 23,000 |
| lactose | 24,000 | — |
| maltose | 23,500 | — |
| galactose | 31,300 | — |
| glucose | 41,000 | — |
| sorbitol | 24,000 | — |
| mannitol | 33,000 | — |
| inositol | 21,000 | — |
| starch | 33,990 | — |

EXAMPLE 33

If, in a mix according to Example 28, the glycerine is replaced by glucose, culture solutions containing 330 AIU/ml are obtained.

EXAMPLE 34

If, in a mix according to Example 28, the starch is replaced by glucose, culture solutions containing 660 AIU/ml are obtained.

EXAMPLE 35

If, in mixes according to Example 29, NZ-amines are replaced by other complex sources of nitrogen, culture solutions containing the following amylase inhibitor units are obtained after 3 days' fermentation:

| Substitute | AIU/ml |
|---|---|
| soya flour | 13,500 |
| fish solubles | 16,800 |
| tryptone | 25,200 |
| meat extract | 32,700 |
| pharmamedia | 23,100 |

EXAMPLE 36

If a mix according to Example 29 is inoculated with a morphological variant of the strain SE 50, namely strain SE 50/12, culture broths containing 51,500 AIU/ml are obtained after 3 days' fermentation.

EXAMPLE 37

If five experimental fermenters each containing 8 liters of culture solution according to Example 1, but with 0.1% by volume of Bayer E 100 anti-foaming agent, are each inoculated with 120 ml of a primary culture (obtained according to Example 1) of strain SE 50 and incubated for 65 hours at 28°C. while stirring and aerating, the fermentation mixes are combined and the mycelium is separated off, 24 liters of culture broth containing 13,000 AIU/ml and 6 SIU/ml are obtained. The culture broth is concentrated to 1 liter by evaporating in vacuo at 20 mm Hg and 100°C. bath temperature. The black-colored concentrate was centrifuged for 60 minutes at 15,000 r.p.m., the dark supernatant liquor was applied to an Amberlite IRA 410 column (9 cm $\phi$, 50 cm height, Amberlite IRA 410 acetate, pH 7 in $H_2O$), the column was eluted with 50 ml of $H_2O$/hour and 20 ml of fractions were collected in the fraction collector. The light yellow-colored fractions containing inhibitor (a total of 300 = 6 liters) were combined, concentrated to a 1 liter on a rotary evaporator and added dropwise, with vigorous stirring, to 10 liters of absolute alcohol, whereupon a flocculent, almost white precipitate separates out. The precipitate is filtered off, washed with absolute alcohol and thereafter with ether and dried in vacuo. Yield: 60 g of a white powder containing $3 \times 10^6$ AIU/g and 400 SIU/g.

EXAMPLE 38

The bulk of the inactive concomitant substances, especially the dark dyestuff, can also be separated off by precipitation with an equal volume of methanol. For this purpose, 26 liters of the centrifuged culture broth (produced according to Example 37, but with 0.02% by volume of Bayer Silicone E antifoaming agent) (43,000 AIU/ml) are concentrated to 1.2 liters by evaporation in vacuo at 20 mm Hg and 100°C. bath temperature. The deep black solution is treated with an equal volume (1.2 liters) of methanol while stirring, whereupon a flocculent black precipitate forms. It is filtered through a fluted filter and the brown filtrate (2.2 liters) is added dropwise to 10 liters of the dry spirit, while stirring vigorously. A light brown precipitate forms, which is filtered off, washed with acetone and ether and dried in vacuo. Yield: 185 g of a light ochre-colored powder containing 3,700 AIU/mg.

For further purification, the entire precipitate (185 g) is dissolved in 250 ml of water and the dark brown solution is passed over a $5 \times 75$ cm column of Amberlite IRA 410 (acetate form, pH 7). The column is eluted with water, the first 500 ml of eluate are discarded as first runnings and the next 5,000 ml of almost colorless eluate contain the inhibitor activity. They are concentrated to 200 ml on a rotary evaporator and the inhibitor is obtained therefrom by adding the solution dropwise to 2 liters of absolute ethyl alcohol, filtering off the precipitate, washing with ethanol and ether and drying in vacuo. Yield: 80 g of a white powder containing 8,000 AIU/mg.

EXAMPLE 39

If a 1 liter Erlenmeyer flask containing 120 ml of a nutrient solution according to Example 4 is inoculated with 2 ml of a primary culture of the strain SE 55 (manufactured according to Example 4) and the culture is incubated for 6 days on a rotary shaking machine at 28°C., a culture broth containing 30 AIU/ml and 0.15 MIU/ml and 0.5 SIU/ml is obtained after separating off the mycelium.

If the mycelium is extracted in accordance with Example 20, an extract containing 15 AIU/ml, 0.17 MIU/ml and 0.5 SIU/ml is obtained.

EXAMPLE 40

If Example 39 is followed, but using a nutrient solution according to Example 1, a culture solution containing 60 AIU/ml, 0.16 MIU/ml and 0.65 SIU/ml and a mycelium extract containing 30 AIU/ml and 0.16 MIU/ml and 0.33 SIU/ml are obtained.

EXAMPLE 41

If a nutrient solution according to Example 39 is inoculated from a sloping test-tube culture on oatmeal agar of the strain SS 26, and the culture is incubated in accordance with Example 40 for 5 days, an extract containing 0.14 MIU/ml is obtained after separating off the culture solution after extraction of the mycelium according to Example 21.

EXAMPLE 42

If Example 41 is followed using a culture of the strain SS 45, a mycelium extract containing 0.1 MIU/ml is obtained.

EXAMPLE 43

If Example 41 is followed using a culture of the strain SS 53, a culture broth containing 0.05 MIU/ml and a mycelium extract containing 0.07 MIU/ml is obtained.

EXAMPLE 44

If a 1 liter Erlenmeyer flask is inoculated with 120 ml of a nutrient solution of composition: 0.5% Bactopeptone, 0.5% meat extract, 0.2% yeast extract, 0.03% casein hydrolysate, 1% i-inositol, 1% sorbitol, 1% D-mannitol, 1% glucose, 0.1% $K_2HPO_4$, 0.05% $MgSO_4$, 0.05% KCl and 0.01% $FeSO_4$, pH adjusted to 7.2, is inoculated from a sloping agar culture (manufactured according to Example 1) of the strain SS 51, a culture solution containing 0.072 MIU/ml and a mycelium extract (manufactured according to Example 21) containing 0.054 MIU/ml are obtained after culture on a rotary shaking machine at 28°C. for 7 days.

EXAMPLE 45

If a nutrient solution according to Example 4 is inoculated from a sloping test-tube culture on oatmeal agar of the strain St 19 and is incubated for three days in accordance with Example 4, a culture solution containing 20 AIU/ml is obtained after separating off the mycelium.

EXAMPLE 46

Experimental technique for demonstrating the action of glycoside-hydrolase inhibitors in rats and man To produce alimentary hyperglycemia and hyperinsulinemia after feeding with carbohydrate, rats ($n = 6$) are given 2.5 g of starch or maltose or sucrose as a solution or suspension/kg, administered orally (control animals). Batches of six other rats receive, additionally to one of the above-mentioned carbohydrates, a glycoside-hydrolase inhibitor in the dosage indicated, administered orally. The blood sugar in the blood from the retro-orbital venous plexus is determined at short intervals after the administration of the carbohydrate by means of the Auto-Analyser [Technicon, according to Hoffman: J. biol. Chem. 120, 51 (1937)].

To produce an alimentary hyperglycemia in man, 50 g of starch/Vp. are administered orally as an aqueous suspension. The blood sugar is determined immediately before the start of the experiment, and at short intervals thereafter, in the capillary blood from the fingertip, in the way described above. In a further experiment, the active substance is added to the starch suspension.

The insulin is determined at short intervals after the administration of the carbohydrate, in the serum of batches of six rats of which one group is given 2.5 g of starch/kg, administered orally (control) and the other groups are additionally given a glycoside-hydrolase inhibitor.

The determination of insulin in the serum is carried out by radio-immunology, based on the double antibody method of Hales and Randle [Biochem. J. 88, 137 (1963)].

Determination of starch in the gestrointestinal tract of rats was carried out at short intervals after oral administration of 300 mg starch/rat. To this purpose, the individual sections of the digestive tract were, after sacrifice of the animal, prepared and washed, and the undigested starch contained in them determined as glucose after acid hydrolysis.

Table 1 (Example 46)

Blood glucose in mg% (mean value ± 1s) of fasting rats at various times after oral administration of starch ± active substance from Example 5.

|  | 15 | 60 mins. |
|---|---|---|
| control without starch | 61 ± 16 | 70 ± 3.4 |
| control with starch | 140 ± 11 | 145 ± 15 |
| starch + 25,000 AIU/kg | 106 ± 20 | 128 ± 11 |

Table 2 (Example 46)

Blood glucose in mg% (mean value ± 1s) of fasting rats at various times after oral administration of starch ± active substance from Example 14.

|  | 15 | 30 | 60 mins. |
|---|---|---|---|
| control without starch | 72 ± 8.5 | 78 ± 12 | 69 ± 12 |
| control with starch | 159 ± 28 | 153 ± 36 | 164 ± 7.9 |
| starch + 25,000 AIU/mg | 95 ± 3.7 | 95 ± 8.7 | 96 ± 7.2 |

Table 3 (Example 46)

Blood glucose in mg% (mean value ± 1s) of fasting rats at various times after oral administration of starch ± active substance from Example 37.

|  | 15 | 30 | 60 mins. |
|---|---|---|---|
| control without starch | 72 ± 8.5 | 78 ± 12 | 69 ± 12 |
| control with starch | 159 ± 28 | 153 ± 36 | 164 ± 7.9 |
| starch + 25,000 AIU/kg | 83 ± 6.5 | 105 ± 5.2 | 104 ± 6.5 |

$P < 0.01 \quad P < 0.001$ against control with carbohydrate

Table 4 (Example 46)

Blood glucose in mg% of a healthy test person at various times after oral administration of starch ± active substance from Example 37.

|  | 0 | 15 | 30 | 60 | 90 mins. |
|---|---|---|---|---|---|
| starch without active substance | 106 | 128 | 150 | 146 | 136 |
| starch + 60,000 AIU/Vp | 100 | 112 | 108 | 110 | 104 |

Table 5 (Example 46)

Blood glucose in mg% (mean value ± 1s) of fasting rats at various times after oral administration of maltose ± active substance from Example 10.

|  | 15 | 30 | 60 mins. |
|---|---|---|---|
| control without maltose | 70 ± 6.7 | 81 ± 15 | 72 ± 9.6 |
| control with maltose | 160 ± 13 | 153 ± 11 | 172 ± 13 |
| maltose + 1.5 MIU | 120 ± 13 | 124 ± 12 | 134 ± 9.4 |

Table 6 (Example 46)

Blood glucose in mg% (mean value ± 1s) of fasting rats at various times after oral administration of sucrose ± active substance from Example 14.

|  | 15 | 30 | 60 mins. |
|---|---|---|---|
| control with sucrose | 61 ± 16 | 77 ± 4.7 | 70 ± 3.4 |
| control with sucrose | 125 ± 14 | 129 ± 7.9 | 135 ± 8.5 |
| sucrose + 50 SIU/kg | 104 ± 4.1 | 116 ± 8.4 | 113 ± 3 |

-------- $P < 0.05$ _____ $P < 0.01$ ===== $P < 0.001$ { against control with carbohydrate Table 7 (Example 46)

Serum insulin in μU/ml (means value ± 1s) of fasting rats at various times after oral administration of 2.5 g of starch ± active substance from Example 14; n = 6.

The serum insulin of fasting rats without being given starch was 6 ±1μU/ml in this experiment.

| Mins. after administration of starch | Starch control | Starch + 10,000 AIU/kg |
|---|---|---|
| 5 | 52 ± 29 | 17 ± 8 |
| 10 | 72 ± 20 | 15 ± 4 |
| 20 | 44 ± 28 | 16 ± 7 |
| 30 | 25 ± 8 | 17 ± 3 |
| 45 | 30 ± 5 | 13 ± 6 |
| 60 | 21 ± 8 | 13 ± 8 |
| 120 | 9 ± 3 | 10 ± 3 |
| 180 | 8 ± 2 | 9 ± 2 |

Table 8 (Example 46)

Serum insulin in μU/ml (mean value ± 1s) of fasting rats at various times after oral administration of 2.5 g of starch ± active substance from Example 37; n=6.

The serum insulin of fasting rats without being given starch was 6 ± 1μU/ml in this experiment.

| Mins. after administration of starch | Starch control | Starch + 10,000 AIU/kg |
|---|---|---|
| 5 | 52 ± 29 | 18 ± 8 |
| 10 | 72 ± 20 | 24 ± 11 |
| 20 | 44 ± 28 | 11 ± 5 |
| 30 | 25 ± 8 | 13 ± 3 |
| 45 | 30 ± 5 | 18 ± 7 |
| 60 | 21 ± 8 | 15 ± 5 |
| 120 | 9 ± 3 | 13 ± 5 |
| 180 | 8 ± 2 | 11 ± 5 |

Figure 2:
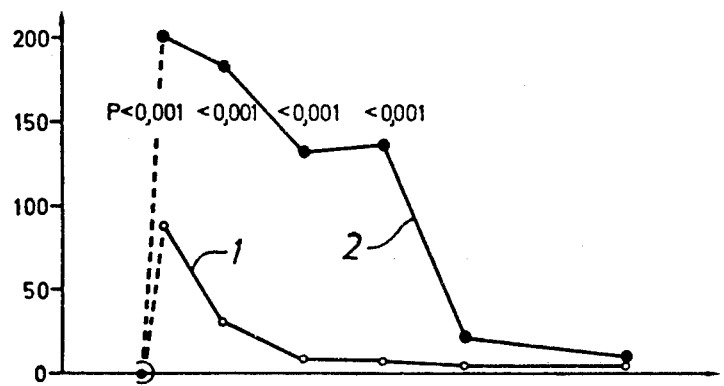
Figure 3:
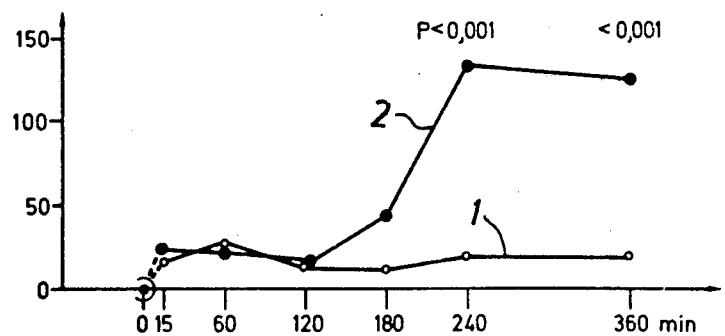

---- $P < 0.05$ _____ $P < 0.01$ ====== $P < 0.001$ { against control with carbohydrate FIGS. 1 to 3 (Example 46)

FIGS. 1 to 3 show the average content of starch in mg (ordinate)/rat (n = 6) in the stomach (FIG. 1), small intestine (FIG. 2) and large intestine ((FIG. 3) at different times (abscissa), after oral application of 300 mg raw wheat starch/rat by a throat probe. In FIGS. 1 to 3 curves 1 demonstrate the result for the controls (Group 1), which were given starch without amylase inhibitor, while the curves 2 demonstrate the result for animals which received an equal dose of starch with addition of 1000 AIU amylase inhibitor (Group 2).

Result:

The content of wheat starch is significantly smaller in the stomach (FIG. 1) 15 + 60 minutes after application (P<0.001 to P <0.02) in Group 2 with amylase inhibitor than in Group 1. The quicker passage of starch through the stomach after addition of amylase inhibitor can also be seen from FIG. 2. In this case the content of starch in the small intestine of Group 2 is significantly (P<0.001) raised after 150–180 minutes. FIG. 3 shows that starch reaches the large intestine of rats undigested, if amylase inhibitor is added to the starch in the stated dose.

FIGS. 4 to 6 (Example 46)

In FIGS. 4 to 6 are shown the alteration of blood glucose in mg/100 ml (ordinate) (FIG. 4), the concentration of immunologically reacting insulin in μU/ml serum (ordinate) (FIG. 5), and the concentration of unesterified fatty acids in micro equivalents/liter of plasma (ordinate) (FIG. 6), against the initial value (0) as dependent on time (abscissa), after oral application of 60 g cooked starch for a human experimental subject. Curve 1 shows the course of the stated parameters (blood sugar, serum insulin, plasma UFA) in the control experiment. Curve 2 shows the change of these parameters after administration of the same dose of starch with the addition of 0.25 mg. AIU amylase inhibitor, curve 3 the changes in the stated parameters after addition of 0.5 mega AIU amylase inhibitor to 60 g cooked starch per person.

Results:

After temporary hyperglycemia between 0 + 30 minutes in FIG. 4 the blood glucose falls after 45–180 minutes to significantly under the initial value. As a result of the initial hyperglycemia the concentration of insulin in the serum in the control experiment (curve 1) climbs steeply. The addition of 0.25 (curve 2) or 0.5 mega AIU (curve 3) to the starch has the effect that the hypoglycemia (FIG. 4) as well as the hyperinsulinemia (FIG. 5) is quickly weakened. The ratio of unesterified fatty acids in the plasma is substantially equal in all three experiments.

EXAMPLE 47

Erlenmeyer flasks containing the medias given in the Table, are inoculated with the corresponding strains and shaken at the stated temperature on a rotary shaker. Thus are obtained, after several days, culture solutions, and, after working up according to Example 21, mycelium extracts, which have the activities given in the Table.

Table (Example 47)

| Strain Number | | | Culture Solutions and Conditions of Growth | | | | |
|---|---|---|---|---|---|---|---|
| Laboratory Reference | Collection No. | Strain Name | See Example | Quantity ml | In Erlenmeyer Flask | Growth Temperature | Culture Period (Days) |
| ST 50 | CBS 693.69 | Streptomyces heimii | 4 | 30 | 200 | 28 | 4 |
| ST 67 | CBS 432.59 | Streptomyces tendae | 44 | 30 | 200 | 28 | 4 |
| ST 45 | CBS 434.51 | Streptomyces aureofaciens | 4 | 30 | 200 | 28 | 4 |
| RT 36 | CBS 228.65 | Chainia rubra | 44 | 30 | 200 | 28 | 4 |
| RT 33 | CBS 295.66 | Chainia poonensis | 44 | 30 | 200 | 28 | 5 |
| ST 12 | NRRL B-2286 | Streptomyces murinus | 1 | 30 | 200 | 28 | 3 |
| ST 51 | CBS 498.68 | Streptomyces fradiae | 44 | 30 | 200 | 28 | 4 |
| ST 3 | NRRL 2580 | Streptomyces chrysomallus | 4 | 30 | 200 | 28 | 5 |
| ST 1 | ATCC 11523 | Streptomyces chrysomallus | 4 | 30 | 200 | 28 | 5 |
| SS 55 | CBS 624.71 | Streptosporangium roseum | 1 | 120 | 1000 | 28 | 6 |
| SS 59 | CBS 623.71 | Streptosporangium amethystogenes | 1 | 120 | 1000 | 28 | 6 |
| SS 62 | CBS 625.71 | Streptosporangium roseum | 1 | 120 | 1000 | 28 | 6 |
| AT 8 | KCC-A 0027 | Streptosporangium viridalbum | 4 | 120 | 1000 | 28 | 4 |
| AT 11 | KCC-A 0025 | Streptosporangium album | 4 | 120 | 1000 | 28 | 4 |
| AT 13 | CBS 190.64 | Ampullariella campanulata | 4 | 120 | 1000 | 28 | 6 |
| AT 14 | CBS 193.64 | Ampullariella regularis | 4 | 120 | 1000 | 28 | 4 |
| SE 89 | CBS 619.71 | Ampullariella spec. | 1 | 120 | 1000 | 28 | 6 |
| SE 100 | CBS 622.71 | Planomonospora spec. | 1 | 120 | 1000 | 28 | 6 |

| Strain Number | | | Activity of Culture Filtrates U/ml | | |
|---|---|---|---|---|---|
| Laboratory Reference | Collection No. | Strain Name | Amylase Inhibition | Maltase Inhibition | Saccharase Inhibition |
| ST 50 | CBS 693.69 | Streptomyces heimii | | | 0.06 |
| ST 67 | CBS 432.59 | Streptomyces tendae | | 0.020 | 0.25 |
| ST 45 | CBS 434.51 | Streptomyces Aureofaciens | | 0.002 | |
| RT 36 | CBS 228.65 | Chainia rubra | | 0.005 | |
| RT 33 | CBS 295.66 | Chainia poonensis | | 0.003 | |
| ST 12 | NRRL B-2286 | Streptomyces murinus | 500 | 0.008 | |
| ST 51 | CBS 498.68 | Streptomyces fradiae | 70 | | |
| ST 3 | NRRL 2580 | Streptomyces chrysomallus | 20 | | |
| ST 1 | ATCC 11523 | Streptomyces chrysomallus | 20 | | |
| SS 55 | CBS 624.71 | Streptosporangium roseum | | | |
| SS 59 | CBS 623.71 | Streptosporangium amethystogenes | | | |
| SS 62 | CBS 625.71 | Streptosporangium roseum | | | |
| AT 8 | KCC-A 0027 | Streptosporangium viridalbum | | | |
| AT 11 | KCC-A 0025 | Streptosporangium album | | | |
| AT 13 | CBS 190.64 | Ampullariella campanulata | 2000 | | |
| AT 14 | CBS 193.64 | Ampullariella regularis | 500 | | |
| SE 89 | CBS 619.71 | Ampullariella spec. | | | |
| SE 100 | CBS 622.71 | Planomonospora spec. | 50 | | |

| Strain Number | | | Activity of the Mycelium Extract According to Example 21 (U/ml) | | |
|---|---|---|---|---|---|
| Laboratory | Collection | Strain Name | Amylase Inhibition | Maltase Inhibition | Saccharase Inhibition |

Table (Example 47)-continued

| Strain Number | | | Culture Solutions and Conditions of Growth | | | | |
|---|---|---|---|---|---|---|---|
| Laboratory Reference | Collection No. | Strain Name | See Example | Quantity ml | In Erlenmeyer Flask | Growth Temperature | Culture Period (Days) |
| ST 50 | CBS 693.69 | Streptomyces heimii | | | | | |
| ST 67 | CBS 432.59 | Streptomyces tendae | | | | | |
| ST 45 | CBS 434.51 | Streptomyces aureofaciens | | | | | |
| RT 36 | CBS 228.65 | Chainia rubra | | | | | |
| RT 33 | CBS 295.66 | Chainia poonensis | | | | | |
| ST 12 | NRRL B-2286 | Streptomyces murinus | | | | | |
| ST 51 | CBS 498.68 | Streptomyces fradiae | | | | | |
| ST 3 | NRRL 2580 | Streptomyces chrysomallus | | | | | |
| ST 1 | ATCC 11523 | Streptomyces chrysomallus | | | | | |
| SS 55 | CBS 624.71 | Streptosporangium roseum | | 100 | | | |
| SS 59 | CBS 623.71 | Streptosporangium amethystogenes | | 70 | | | |
| SS 62 | CBS 625.71 | Streptosporangium roseum | | 150 | | | |
| AT 8 | KCC-A 0027 | Streptosporangium viridalbum | | 150 | | | |
| AT 11 | KCC-A 0025 | Streptosporangium album | | 100 | | | |
| AT 13 | CBS 190.64 | Ampullariella campanulata | | | | | |
| AT 14 | CBS 193.64 | Ampullariella regularis | | | | | |
| SE 89 | CBS 619.71 | Ampullariella spec. | | 2000 | | | |
| SE 100 | CBS 622.71 | Planomonospora spec. | | 50 | | | |
| AT 4 | CBS 191.64 | Ampullariella digitata | 4 | 120 | 1000 | 28 | 6 |
| AT 9 | KCC-A 0028 | streptosporangium vulgare | 4 | 120 | 1000 | 28 | 5 |
| AT 10 | ATCC 19190 | Streptosporangium indianensis | 1 | 120 | 1000 | 28 | 4 |
| AT 10 | ATCC 19190 | Streptosporangium indianensis | 44 | 120 | 1000 | 28 | 5 |
| SE 103 | CBS 616.71 | Actinoplanes spec. | 1 | 120 | 1000 | 28 | 4 |
| HN 6 | CBS 602.71 | Actinobifida chromogena | 44 | 120 | 1000 | 50 | 4 |
| HN 2 | CBS 603.71 | Actinobifida chromogena | 44 | 120 | 1000 | 50 | 5 |
| AT 2 | CBS 367.66 | Actinoplanes utahensis | 4 | 120 | 1000 | 28 | 4 |
| SE 101 | CBS 621.71 | Planomonospora parontospora | 1 | 120 | 1000 | 28 | 6 |
| SK 2 | CBS 620.71 | Pilimelia spec. | 1 | 120 | 1000 | 28 | 7 |
| SE 82 | CBS 615.71 | Actinoplanes spec. | 4 | 120 | 1000 | 28 | 5 |
| | | | 1 | 120 | 1000 | 28 | 5 |
| SE 45 | CBS 618.71 | Ampullariella spec. | 4 | 120 | 1000 | 28 | 4 |
| SA 28 | CBS 617.71 | Ampullariella digitata | 1 | 120 | 1000 | 28 | 5 |
| SA 8 | CBS 611.71 | Actinoplanes spec. | 4 | 120 | 1000 | 28 | 5 |
| AT 7 | ATCC 12428 | Streptosporangium roseum | 4 | 120 | 1000 | 28 | 4 |

| Strain Number | | | Activity of the Culture Filtrate U/ml | | |
|---|---|---|---|---|---|
| Laboratory Reference | Collection No. | Strain Name | Amylase Inhibition | Maltase Inhibition | Saccharase Inhibition |
| AT 4 | CBS 191.64 | Ampullariella digitata | | 0.003 | 0.5 |
| AT 9 | KCC-A 0028 | Streptosporangium vulgare | | | 0.4 |
| AT 10 | ATCC 19190 | Streptosporangium indianensis | | | 0.5 |
| AT 10 | ATCC 19190 | Streptosporan- | | | 0.3 |

Table (Example 47)-continued

| Strain Number | | | Activity of the Culture Filtrate U/ml | | |
|---|---|---|---|---|---|
| Laboratory Reference | Collection No. | Strain Name | Amylase Inhibition | Maltase Inhibition | Saccharase Inhibition |
| SE 103 | CBS 616.71 | Actinoplanes spec. gium indianensis | | | |
| HN 6 | CBS 602.71 | Actinobifida chromogena | | | |
| HN 2 | CBS 603.71 | Actinobifida chromogena | | | |
| AT 2 | CBS 367.66 | Actinoplanes utahensis | | 0.003 | |
| SE 101 | CBS 621.71 | Planomonospora parontospora | | | |
| SK 2 | CBS 620.71 | Pilimelia spec. | | | |
| SE 82 | CBS 615.71 | Actinoplanes spec. | 200 3000 | 0.010 0.008 | 0.8 0.8 |
| SE 45 | CBS 618.71 | Ampullariella spec. | | | |
| SA 28 | CBS 617.71 | Ampullariella digitata | | 0.002 | |
| SA 8 | CBS 611.71 | Actinoplanes spec. | | | |
| AT 7 | ATCC 12428 | Streptosporangium roseum | | | |

| Strain Number | | | Activity of Mycelium Extract According to Example 21 (U/ml) | | |
|---|---|---|---|---|---|
| Laboratory Reference | Collection No. | Strain Name | Amylase Inhibition | Maltase Inhibition | Saccharase Inhibition |
| AT 4 | CBS 191.64 | Ampullariella digitata | | | |
| AT 9 | KCC-A 0028 | Streptosporangium vulgare | | 0.004 | 1.5 |
| AT 10 | ATCC 19190 | Streptosporangium indianensis | | | |
| AT 10 | ATCC 19190 | Streptosporangium indianensis | | | 0.3 |
| SE 103 | CBS 616.71 | Actinoplanes spec. | | | 0.5 |
| HN 6 | CBS 602.71 | Actinobifida chromogena | | | 1.5 |
| HN 2 | CBS 603.71 | Actinobifida chromogena | | | 3.0 |
| AT 2 | CBS 367.66 | Actinoplanes utahensis | | | |
| SE 101 | CBS 621.71 | Planomonospora parontospora | | 0.006 | |
| SK 2 | CBS 620.71 | Pilimelia spec. | | | 0.8 |
| SE 82 | CBS 615.71 | Actinoplanes spec. | 2000 35000 | 0.010 0.003 | 0.6 0.5 |
| SE 45 | CBS 618.71 | Ampullariella spec. | | | 0.2 |
| SA 28 | CBS 617.71 | Ampullariella digitata | | 0.003 | |
| SA 8 | CBS 611.71 | Actinoplanes spec. | 200 | | |
| AT 7 | ATCC 12428 | Streptosporangium roseum | 50 | | |

We claim:

1. A method of inhibiting the reaction of carbohydrates and carbohydrate-splitting enzymes of the digestive tract which comprises conducting the reaction of said carbohydrates and carbohydrate-splitting enzymes of the digestive tract in the presence of an enzyme inhibitor for said carbohydrate-splitting enzymes of the digestive tract derived from a strain of microorganism of the order Actinomycetales, wherein said enzyme inhibitor:

a. is substantially heat-stable at neutral pH values;
b. is stable to acid at pH 2;
c. is stable to alkali at pH 12;
d. is slowly dialyzable;
e. is not inactivated by trypsin or pepsin;
f. does not inhibit trypsin or pepsin;
g. is not receptive to protein dyes;
h. is free from characteristic UV absorption up to 250 nm.;
i. is not inhibited by urea or $\beta$-mercaptoethanol;
j. is of molecular weight 500–6000; and
k. yields a monosaccharide on hydrolytic splitting.

* * * * *

UNITED STATES PATENT OFFICE
CERTIFICATE OF CORRECTION

Page 1 of 2

Patent No. 4,013,510     Dated March 22, 1977

Inventor(s) Werner Frommer et al

It is certified that error appears in the above-identified patent and that said Letters Patent are hereby corrected as shown below:

Column 4, line 32, "amuylase" should be --amylase--.

Column 13, under "SA 8", across from "Melanine", "Gel 30" should be --Gel +--.

Between Columns 13 and 14 and Columns 15 and 16, the heading "Streptosporangium amethystogenes roseum" should be --Streptosporangium amethystogenes--.

Columns 14 and 16, in the heading after "Streptosporangium" insert -- roseum --.

Column 27, lines 47-50, the equation should read:

$$\text{starch or glycogen} \xrightarrow{\text{amylase}} \text{maltose} \xrightarrow{\text{maltase}} \text{glucose}$$

$$\text{sucrose} \xrightarrow{\text{saccharase}} \text{glucose} + \text{fructose}$$

Column 41, in Table 6, first line of table, "control with sucrose" should be --control without sucrose--.

Columns 45 and 46, remove the first two lines of heading. (Take out line with "Strain Number" and line with "Laboratory Reference")

UNITED STATES PATENT AND TRADEMARK OFFICE
CERTIFICATE OF CORRECTION

PATENT NO. : 4,013,510

DATED : March 22, 1977

INVENTOR(S) : Werner Frommer et al.

It is certified that error appears in the above—identified patent and that said Letters Patent is hereby corrected as shown below:

Between Columns 47 and 48, last chart, across from "SE 82" under "Anylase Inhibition", "2000" should read -- 200 --.

Signed and Sealed this

Twenty-ninth Day of April 1980

[SEAL]

Attest:

Attesting Officer

SIDNEY A. DIAMOND

Commissioner of Patents and Trademarks